(12) United States Patent
Maltezos et al.

(10) Patent No.: US 8,479,538 B2
(45) Date of Patent: *Jul. 9, 2013

(54) ENHANCING THE OPTICAL CHARACTERISTICS OF A GEMSTONE

(75) Inventors: George Maltezos, Fort Salonga, NY (US); Axel Scherer, Laguna Beach, CA (US); Jeremy Witzens, Del Mar, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/253,678

(22) Filed: Oct. 5, 2011

(65) Prior Publication Data

US 2012/0024010 A1 Feb. 2, 2012

Related U.S. Application Data

(63) Continuation of application No. 11/635,386, filed on Dec. 6, 2006, now Pat. No. 8,033,136.

(60) Provisional application No. 60/748,337, filed on Dec. 6, 2005, provisional application No. 60/801,579, filed on May 18, 2006, provisional application No. 60/808,635, filed on May 26, 2006, provisional application No. 60/809,284, filed on May 30, 2006, provisional application No. 60/810,948, filed on Jun. 5, 2006, provisional application No. 60/812,358, filed on Jun. 9, 2006.

(51) Int. Cl.
*A44C 17/00* (2006.01)

(52) U.S. Cl.
USPC ............................................................. 63/32

(58) Field of Classification Search
None
See application file for complete search history.

(56) References Cited

U.S. PATENT DOCUMENTS

| 484,934 | A | 10/1892 | Jacobson |
| 1,354,471 | A | 10/1920 | Doner |
| 2,081,483 | A | 5/1937 | Evanda |
| 2,511,510 | A | 6/1950 | Mukai |
| 4,030,317 | A | 6/1977 | Rogell |
| 4,425,769 | A | 1/1984 | Hakoune |
| 4,809,417 | A | 3/1989 | Normann |
| 5,044,123 | A | 9/1991 | Hoffman |

(Continued)

FOREIGN PATENT DOCUMENTS

| DE | 92 07 571 U1 | 8/1992 |
| EP | 0 648 445 A1 | 4/1995 |

(Continued)

OTHER PUBLICATIONS

Bragg, W. L., "The Diffraction of Short Electromagnetic Waves by a Crystal," Proceedings of the Cambridge Philosophical Society, vol. XVII, Oct. 28, 1912-May 18, 1914, Cover Page and pp. 43-57.

(Continued)

*Primary Examiner* — Jack W. Lavinder
(74) *Attorney, Agent, or Firm* — Knobbe, Martens, Olson and Bear, LLP

(57) ABSTRACT

Various embodiments described herein comprise a gemstone or other piece of jewelry, which incorporates one or more diffractive optical elements to enhance the fire displayed by the gemstone. In certain embodiments, the diffractive optical element comprises a diffraction grating etched on one or more facets of the gemstone.

24 Claims, 14 Drawing Sheets

U.S. PATENT DOCUMENTS

| | | | |
|---|---|---|---|
| 5,612,102 A * | 3/1997 | Nakama | 428/15 |
| 5,966,673 A | 10/1999 | Shannon | |
| 8,033,136 B2 | 10/2011 | Maltezos et al. | |
| 2005/0011225 A1 | 1/2005 | Kearnes et al. | |
| 2005/0213077 A1 | 9/2005 | Sasian | |
| 2006/0190292 A1 | 8/2006 | Reinitz | |
| 2007/0043587 A1 | 2/2007 | Reinitz | |
| 2007/0157667 A1 | 7/2007 | Maltezos | |
| 2009/0126402 A1 | 5/2009 | Maltezos et al. | |

FOREIGN PATENT DOCUMENTS

| | | |
|---|---|---|
| EP | 2289361 | 3/2011 |
| GB | 2 332 651 A | 6/1999 |
| JP | 62-041605 | 2/1987 |
| KR | 10-1999-0080103 | 4/2000 |
| KR | 10-2001-0105936 | 11/2001 |
| LU | 6/421 | 6/1973 |
| WO | WO 02/31474 A | 4/2002 |
| WO | WO 02/066263 A | 8/2002 |
| WO | WO 2007/067696 | 6/2007 |
| WO | WO 2010/003600 | 1/2010 |

OTHER PUBLICATIONS

International Search Report and Written Opinion for International Application No. PCT/US2008/085078 mailed on Jul. 17, 2009 in 8 pages.

Kunz, G.F.,"Precious Stones, Mineral Resources of the United States," Government Printing Office 1888, Cover Page, Table of Contents in 2 Pages, and pp. 555-571.

Moses, T.M. et al., "A Foundation for Grading the Overall Cut Quality of Round Brilliant Cut Diamonds," Gems & Gemology, vol. 40, No. 3, Fall 2004, pp. 202-228.

Reinitz, I.M. et al., "Modeling the Appearance of the Round Brilliant Cut Diamond: An Analysis of Fire, and More About Brilliance," Gems & Gemology, vol. 37, No. 3, Fall 2001, pp. 174-197.

Search Report, PCT/US2006/046719, Filed December 6, 2006.

Wells, O.C. et al., "Automatic Positioning of Device Electrodes Using the Scanning Electron Microscope," IEEE Transactions on Electron Devices, vol. ED- 12, No. 10, Oct. 1965, pp. 556-563.

Wolf, E.D. et al., "Electron Beam and Ion Beam Fabricated Microwave Switch," IEEE Transactions on Electron Devices, vol. ED-17, No. 6, Jun. 1970, pp. 446-449.

Office Action issued in connection with European Application No. 06 844 964.4, filed on Dec. 6, 2006, mailed on Dec. 22, 2010.

Restriction Requirement issued on Jun. 16, 2009 in connection with U.S. Appl. No. 11/635,386, filed Dec. 6, 2006.

Response to Restriction Requirement issued on Jun. 16, 2009, filed on Jul. 16, 2009 in connection with U.S. Appl. No. 11/635,386, filed Dec. 6, 2006.

Office Action issued on Aug. 28, 2009 in connection with U.S. Appl. No. 11/635,386, filed Dec. 6, 2006.

Response to Office Action issued on Aug. 28, 2009, filed on Jan. 28, 2010 in connection with U.S. Appl. No. 11/635,386.

Final Office Action issued on Apr. 5, 2010 in connection with U.S. Appl. No. 11/635,386, filed Dec. 6, 2006.

Request for Continued Examination and Amendment filed in Response to Final Office Action issued on Apr. 5, 2010, filed on Oct. 4, 2010 in connection with U.S. Appl. No. 11/635,386, filed Dec. 6, 2006.

Office Action issued on Nov. 5, 2010, in connection with U.S. Appl. No. 11/635,386, filed Dec. 6, 2006.

Response to Office Action issued on Nov. 5, 2010, filed on May 4, 2011 in connection with U.S. Appl. No. 11/635,386.

Notice of Allowance issued in connection with U.S. Appl. No. 11/635,386, filed Dec. 6, 2006.

Search Report issued in connection with European Application No. 10188178.7, filed on Dec. 6, 2006, mailed on Jan. 31, 2011.

* cited by examiner

ENHANCING THE OPTICAL CHARACTERISTICS OF A GEMSTONE

CROSS-REFERENCE TO RELATED APPLICATIONS

This application is a continuation of U.S. patent application Ser. No. 11/635,386, filed Dec. 6, 2006, and entitled "ENHANCING THE OPTICAL CHARACTERISTICS OF A GEMSTONE," which claims priority to the following U.S. provisional patent applications: 60/748,337, filed Dec. 6, 2005; 60/801,579, filed May 18, 2006; 60/808,635, filed May 26, 2006; 60/809,284, filed May 30, 2006; 60/810,948, filed Jun. 5, 2006; and 60/812,358, filed Jun. 9, 2006. All of the foregoing applications are hereby incorporated by reference herein in their entirety.

BACKGROUND

1. Field of the Invention

The field of the invention relates to gemstones and jewelry, and more particularly to enhancing the optical characteristics of a gemstone and jewelry.

2. Description of the Related Art

Gemstones are prized for their rarity and beauty. Among gemstones, diamonds, in particular, are highly valued. Apart from their worth in industrial applications, diamonds are considered symbols of love, beauty, and purity in many cultures. When used for their aesthetic quality, diamond crystals are often cut and polished in ways that emphasize certain optical properties such as their brilliance or fire. This is especially true of the round brilliant cut, whose optical properties were studied and mathematically characterized in a paper by Marcel Tolkowsky in 1919.

FIG. 1 illustrates a typical round brilliant cut diamond 100. The round brilliant cut includes an upper crown portion 130. The crown 130 generally has a flat top portion, known as the table 110. The lower portion of the round brilliant cut is the pavilion 150, whose tip is called the culet 160. Very often the crown 130 and the pavilion 150 are separated by a flat girdle 140 of some width to help prevent chipping that might otherwise occur if the crown 130 and pavilion 150 were joined at a sharp angle. The diameter of the round brilliant cut at the girdle 140 is called the spread of the diamond. The round brilliant cut also has a number of generally flat facets 170.

Tolkowsky began his study of the round brilliant cut with a poll of passersby on city streets to determine the crown 130 and pavilion 150 angles and heights, as well as their proportions to the spread 120 and table 110 width, which people found to be the most beautiful. Tolkowsky then undertook a study of the round brilliant cut and showed mathematically that the diamonds which the public found to be most beautiful were those whose angles and proportions resulted in a better balance of brilliance and fire than round brilliant cuts of other dimensions.

The brilliance of the cut refers, in part, to its brightness in terms of the amount of light that it reflects to a face-up observer (viewing the diamond crown 130 perpendicularly to the table 110 surface). Due to the geometry of the round brilliant cut, much of the light that enters the crystal from above is reflected by the walls of the pavilion 150, the pavilion, in effect, acting as a corner reflector, and returned toward an observer through the crown 130. Light that is not reflected back towards the observer is said to have "leaked" out of the diamond.

Fire, in contrast, refers to the rainbow of colors produced by the diamond, noticeable mainly at the crown facets 170. This effect is due to the relatively high dispersion or wavelength dependence of the refractive index of diamond. Dispersion causes light of different wavelengths to be refracted different amounts upon entering the facets of the diamond. These different wavelengths then propagate along separate optical paths through the diamond and also exit the stone at distinct angles as well. Flashes of color may thus be seen at different angles of view. This effect is enhanced as light exits the diamond near the critical angle between the diamond-to-air interface. This strong ability to split white light into its component colors is an important aspect of diamond's attraction as a gemstone, giving it impressive prismatic action that results in the fire of a well-cut stone.

While Tolkowsky calculated "ideal" angles and proportions for a round brilliant cut diamond that gave "the most vivid fire and the greatest brilliancy," he also noted, of the pavilion angle in particular, that although "a greater angle would give better reflection, this would not compensate for the loss due to the corresponding reduction in dispersion." Thus, a round brilliant cut diamond, as well as any other style of cut, faces tradeoffs between brilliance and fire, with the most beautiful cuts achieving a delicate balance between the two. For example, steep crown angles and small tables tend to increase fire (a larger table size means a smaller crown facet area—the part that creates the most dispersion) in a round brilliant cut diamond but also decrease the amount of brilliance. To make matters worse, a diamond cutter must consider many other factors when cutting a particular diamond crystal, which may result in a gem of less beauty than might be possible if the diamond were cut exclusively with its optical properties in mind. These factors include the desire to remove as little material as possible from the rough diamond crystal during the cutting process; the desire to exclude inclusions from the final cut; the desire to target certain carat weights which are typically more sought after by consumers (i.e. ½, 1, 2, carat, etc.); and the desire to use certain high-seller fancy cuts such as princess, marquise, pear, oval, heart, etc. These competing factors generally do not allow a diamond crystal to be cut in such a way as to simultaneously maximize brilliance and fire, or in many instances, to even achieve the "ideal" balance between the two.

SUMMARY OF CERTAIN PREFERRED EMBODIMENTS OF THE INVENTION

Various embodiments are described herein, some of which may be used to increase or control the fire and/or brilliance of a diamond.

One embodiment of the invention comprises a gemstone comprising: a body comprising crystalline material and a diffractive optical element disposed on or in the body. The diffractive optical element comprises a plurality of diffractive features spaced with respect to each other to diffract visible light.

Another embodiment of the invention comprises a gemstone comprising: a body having a surface and a diffractive optical element comprising a plurality of diffractive features patterned in the body or on the surface of the body. The diffractive features are spaced with respect to each other to diffract visible light.

Another embodiment of the invention comprises a method of altering the fire of a gemstone. The method comprises providing a gemstone and forming a diffractive optical element comprising a plurality of diffractive features in or on the gemstone. The diffractive features are spaced with respect to each other to diffract visible light.

Another embodiment of the invention comprises jewelry. The jewelry comprises a body comprising precious metal and a reflective diffractive optical element disposed on or in the body. The reflective diffractive optical element comprises a plurality of diffractive features spaced with respect to each other to diffract visible light.

Another embodiment of the invention comprises a method of simulating the optical properties of a gemstone that includes a diffractive optical element. The method comprises executing a ray-tracing algorithm to determine the propagation of light through the gemstone, and simulating the effect of diffraction of at least a portion of the light from the diffractive optical element.

Another embodiment of the invention comprises a machine-readable medium that, when read by a machine, causes the machine to perform a method. The method comprises executing a ray-tracing algorithm to determine the propagation of light through a gemstone, and simulating the effect of a diffractive optical element in or on the gemstone.

BRIEF DESCRIPTION OF THE DRAWINGS

Example embodiments of gemstones and methods of fabricating diffractive features are illustrated in the accompanying drawings, which are for illustrative purposes only.

DETAILED DESCRIPTION OF THE CERTAIN PREFERRED EMBODIMENTS

Figure 1:
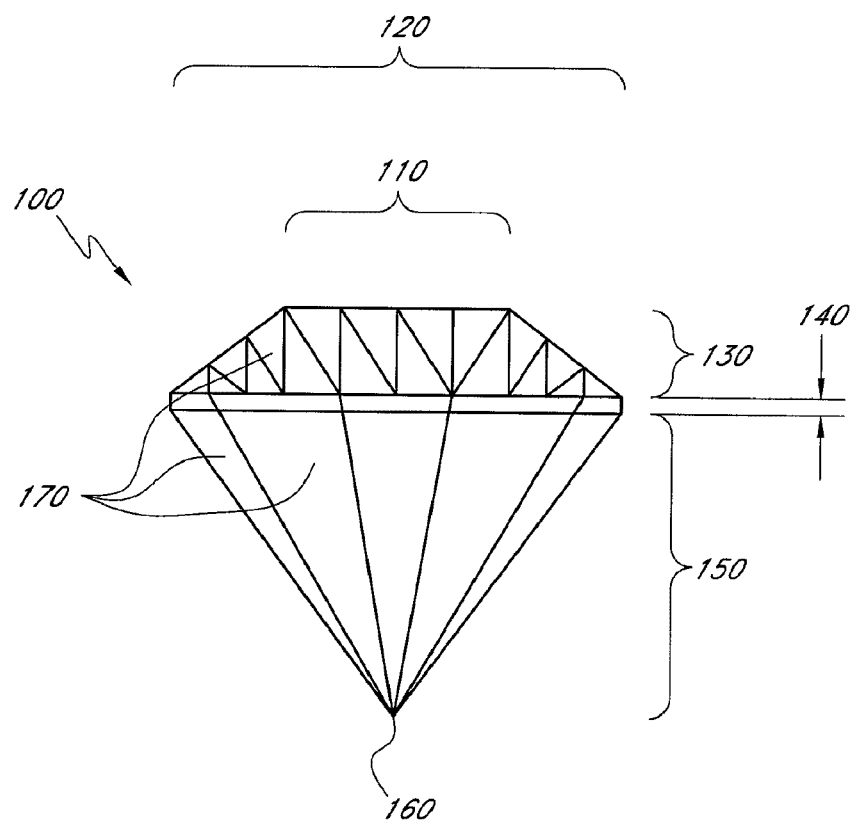
FIG. 1 is a schematic representation of a round brilliant cut diamond.

I. Enhancing Optical Characteristics of Gemstones with Diffractive Elements

As described above, the perceived beauty of a diamond is affected by aspects of its optical properties, such as its brilliance and fire. The optical properties of a diamond can be controlled to some degree by the cut of the diamond. Certain cuts may enhance the brilliance of the diamond, while others may enhance its perceived fire. However, the tradeoff between brilliance and fire makes the "ideal" diamond cut elusive, for to emphasize one optical property is to de-emphasize another, in most cases. Factors related to the desired size and weight of a cut diamond can also influence the resulting optical properties. For example, to achieve a specific weight, the diamond cutter may be forced to use shapes, sizes, or proportions which add little to the beauty of the gem, in terms of its optical properties, and, in some instances, may even worsen it. The result of these tradeoffs is that many cut diamonds do not achieve their full potential for beauty. To put it in other terms, the problem of achieving ideal optical properties for a diamond is over constrained in the sense that there is insufficient flexibility amongst the variables (i.e. cut angles, proportions, size, weight, etc.) to reach a solution which is close to optimal for each of the diamond's optical properties. While embodiments of the invention are described and illustrated primarily in terms of round brilliant gemstone cuts, it should be understood that any type of cut can be used. These may include princess, marquise, baguette, heart, briolette, oval, and pear cuts, to name some examples. Those skilled in the art will be aware of many other cuts which could also be used.

This problem can be solved by the use of modern fabrication techniques to create diffractive optical elements, such as diffraction gratings and other types of arrays of diffractive features, on or into a surface of a diamond. In certain preferred embodiments of the invention, these diffractive optical elements can be patterned onto a gemstone after the gemstone has been cut and polished, though cutting and polishing is not required. Each diffractive optical element may include a number of individual diffractive features, such as grooves, indentations, protrusions, reflective or absorbent markings, or the like. The individual diffractive features can include any structure or features that scatter light, diffract light, selectively modulate or alter the amplitude, or selectively modulate, alter, or shift the phase of incident light, or selectively redirect incident light rays. Furthermore, the individual diffractive features of which any diffractive optical element is comprised need not all be identical; diffractive features of different shapes can be used within a single diffractive optical element to achieve desired optical effects. Accordingly a wide variety of diffractive features, scatter features, phase shift or amplitude modulation features may be used.

These diffractive optical structures can be used to enhance the dispersion, or fire, of a diamond independent of the diamond's cut or shape. In effect, the use of diffractive optical elements adds an additional degree of freedom to the problem of manipulating the optical properties of a diamond, allowing for the creation of more beautiful diamonds. For instance, a diamond could be cut to increase its brilliance with less regard to the impact upon its fire because the fire of the diamond can be enhanced later using the techniques described herein. (The term "cut" is meant to refer to the "macroscopic" facets and features of a gemstone rather than to the microscopic diffractive features described herein.) In the case of a round brilliant cut diamond, brilliance could be emphasized in some cases with a wider table 110 (with respect to a given spread 120), a thinner crown 130, or a smaller culet angle. In other embodiments, the cut of a diamond could be chosen to achieve a desired carat weight and diffractive optical structures could later be used to enhance the cut's optical characteristics, e.g., provide or increase fire. For example, the carat weight of a round brilliant cut diamond could be increased by increasing the size of the table 110, relative to the spread 120. The diffractive optical structures could be used to enhance the optical characteristic, e.g., provide or increase fire.

In addition, much more control can be exerted over the fire characteristics of a diamond by using the principles of the invention than could be achieved by manipulating its cut alone. For example, a diamond could be designed to exhibit intensely different colors when viewed from slightly different angles. In other instances, the diffractive optical elements could be designed such that the diamond exhibits a more understated effect with less intense colors.

It should be understood that while various embodiments will be described primarily in terms of its applications to diamonds, the principles described herein could be equally applied to improve the optical properties of any other gemstone, natural or synthetic, including, but not limited to, crystals, minerals, precious metals, and mineraloids. These may include rubies, sapphires, pearls, and emeralds. Diamonds in particular do, however, possess the advantages of having a high index of refraction, enhancing their potential for brilliance by decreasing the critical angle of total internal reflection (making it much more likely that light will be internally reflected inside a diamond than in other materials with lower refractive indexes). Furthermore, diamonds impart relatively little color filtering to incident light, depending upon the degree and type of impurities present in the diamond crystalline lattice.

Diffractive optical elements can also be applied to other natural and artificial diamond stimulants and clear stones with a relatively high refractive index such as cubic zirconium, zircon, moissanite, topaz, rutile, strontium titanate, spinel, yttrium aluminum garnet, strontium titanate, yttrium aluminum garnet (YAG), gadolinium gallium garnet (GGG), and glass to name only a few examples. Furthermore, the diffractive optical elements could also be applied to other items of jewelry, whether optically transmissive or not (e.g., reflective diffractive structures could be used on opaque materials to add fire). In fact, diffractive optical elements could be applied to any material whose aesthetic appearance can be enhanced by the dispersive effects of diffractive optical elements.

Figure 2:
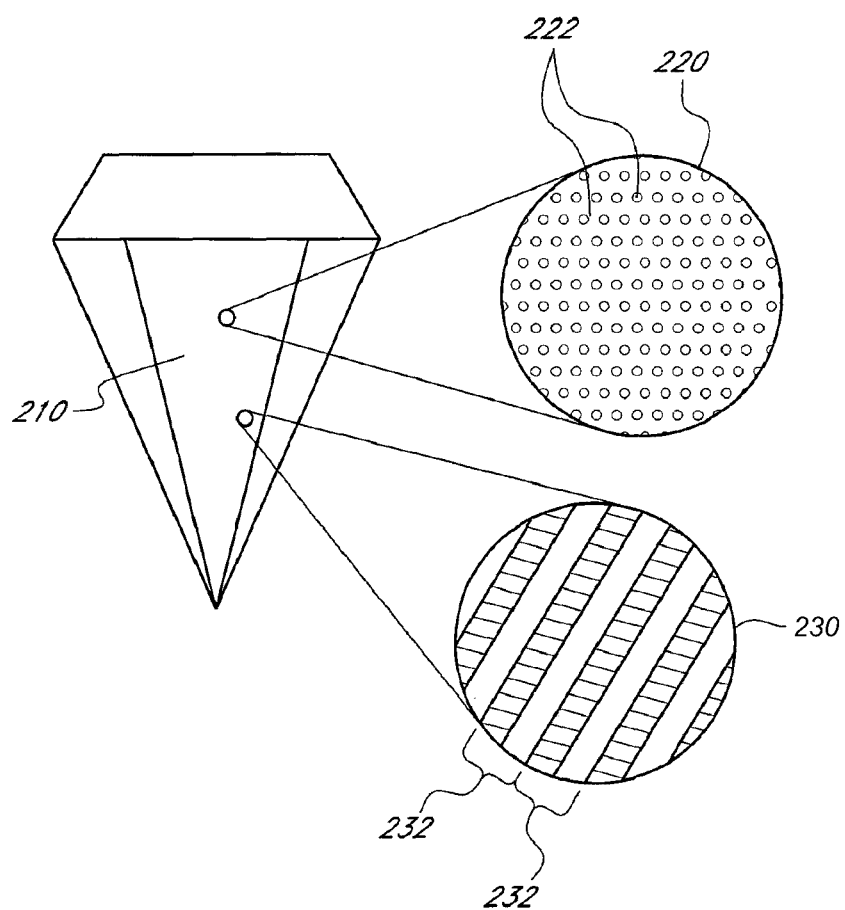
FIG. 2 is a schematic representation of a diamond having patterned thereon diffractive optical elements.

FIG. 2 illustrates a diamond which incorporates artificially patterned diffractive optical elements. The diffractive optical elements are shown in the enlarged insets 220 and 230. In certain preferred embodiments, the diffractive optical elements are located on the surface of a planar facet, such as a facet 210. It should be understood that for purposes of this disclosure, any diffractive optical element disposed in proximity to the surface of a gemstone, whether deposited on the surface or etched into it, for example, shall be considered "on" the surface. In other embodiments, the diffractive optical elements may be located on rounded surfaces of a diamond. In fact, embodiments described herein may make the use of diamond cuts which feature some rounded surfaces, in place of the mainly planar facets on common diamond cuts, more attractive than would otherwise be the case because such rounded surfaces can now be made to exhibit a greater degree of the fire that is generally more characteristic of faceted cuts.

In some embodiments, the diffractive optical elements can be deposited onto the surface of the diamond. In these embodiments, the diffractive structures may comprise a type of material other than the diamond or gemstone (e.g., metal) upon which the structures are deposited. In certain preferred embodiments, however, the diffractive optical elements can be patterned into or on the diamond surface itself using a variety of techniques discussed below. These embodiments can have the characteristic of comprising 100% gemstone material, unlike embodiments in which the diffractive optical elements may be formed out of a material distinct from that of which the gemstone is formed. In still other embodiments, the diffractive optical elements may be located within a diamond, or other optically transmissive gemstone. These structures can be formed using ion implantation techniques or, in other instances, by forming diffractive features in proximity to the surfaces of two or more portions of a gem (e.g. a doublet), which are then joined together such that the diffractive features are positioned within the gem. It is also possible to form diffractive features inside a gemstone by growing an artificial crystal, interrupting the growth, forming the diffractive features on a surface of the crystal (as discussed below), and then continuing the process of growing the crystal.

Inset 220 illustrates a two-dimensional array of diffractive features patterned on the surface of facet 210. The array of diffractive features 220 comprises a triangular lattice of cylindrical indentations 222. In other cases, the diffractive features 222 of the array 220 could be deposited onto the facet 210, for example in the form of cylindrical protrusions. In preferred embodiments, the size and spacing of the individual diffractive features 222 are set so as to diffract light within the visible portion of the electromagnetic spectrum. While the individual diffractive features 222 of the two-dimensional array are shown as being cylindrically shaped, literally any other shape is possible. Different shapes can be chosen based upon ease of manufacture or upon each shape's particular diffractive characteristics (different shapes may result in different relative intensities between the various diffractive orders of the array). Furthermore, a triangular lattice is shown in inset 220, but many others lattice types are suitable, including square lattices or higher order lattices.

In some embodiments, the spacing between diffractive features 222 in the two-dimensional array 220 can be periodic. In other embodiments, however, the spacing between diffractive features can be quasi-periodic, or disordered. In these embodiments, the distances (center-to-center) between diffractive features 222 can be distributed about a mean, or a finite number of means, with a standard deviation that is approximately 2 times the mean, or less. In certain preferred embodiments, the standard deviation can be approximately 1 times the mean, or less. In some embodiments, the mean itself can be approximately in the range of 2-50 microns. In more preferred embodiments, the mean can lie approximately in the range of 4-20 microns. Other patterns and ranges are also possible.

Figure 3:
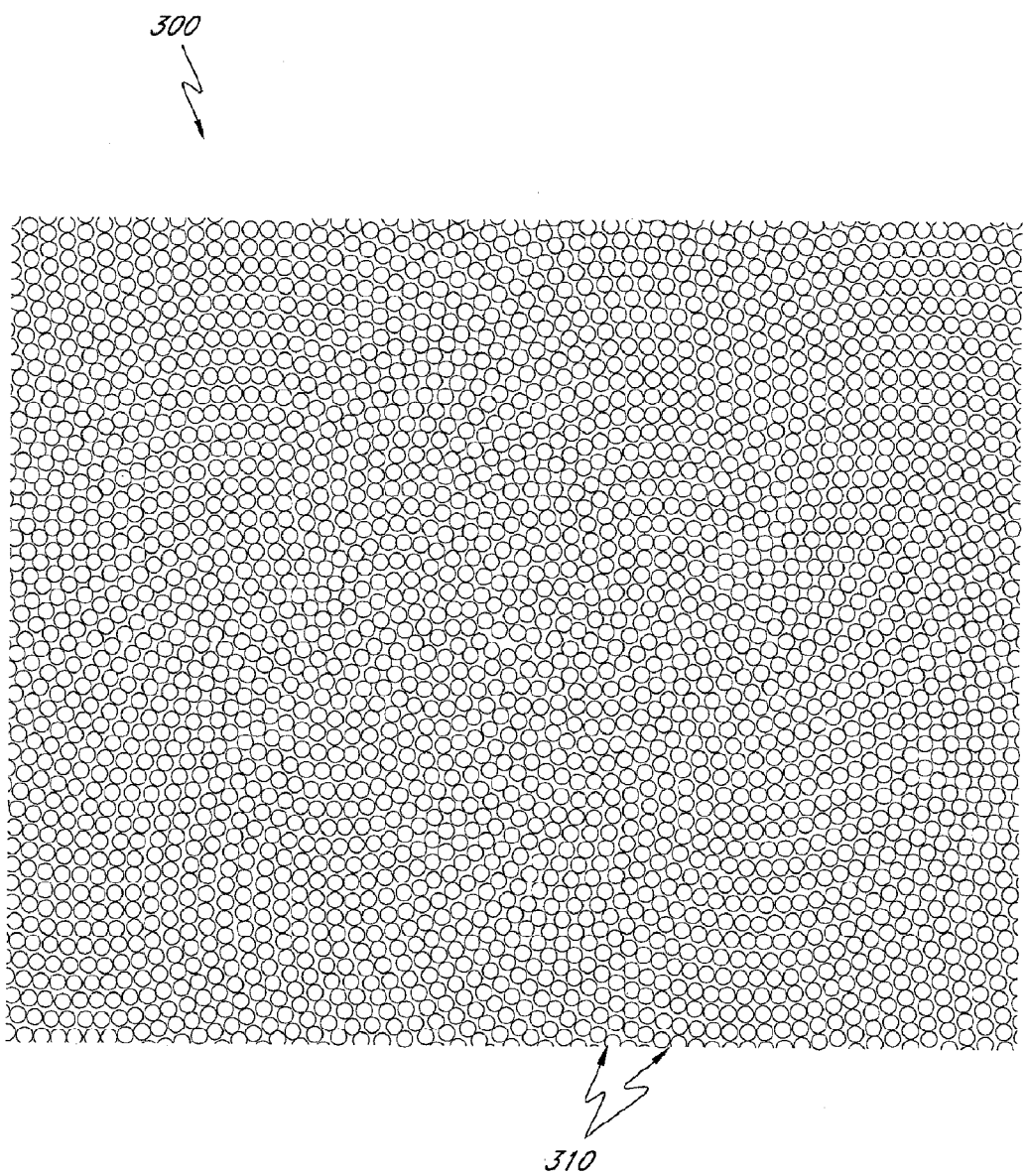
FIG. 3 is a schematic representation of a "sunflower" pattern.

One specific type of two dimensional array that can be used is a "sunflower structure," an example of which is illustrated in FIG. 3. FIG. 3 shows a diffractive optical element 300 which comprises a plurality of individual diffractive features 310. The locations of the diffractive features 310, with respect to a chosen coordinate system, can be calculated according to the following forumula:

$$x_i = P\sqrt{i}\cos(i\phi) \text{ and } y_i = P\sqrt{i}\sin(i\phi) \quad \text{(Equation 1)}$$

where i is an integer and the ordered pair (xi,yi) represents the coordinates of the ith diffractive feature. P and φ are parameters which can be adjusted to alter features of the design such as the mean feature-to-feature spacing, etc. Still other examples of two dimensional arrays that can be used are Archimedean tilings and Penrose tilings, although the configurations should not be limited to the patterns set forth as examples herein. The diffractive optical effect that will result from these structures can be approximated as the Fourier transform of the design itself. Other structures with a local order parameter, or a finite number of local order parameters, are also possible. The diffractive optical element may comprise other arrays of diffractive features such as tilings that include the following: repetition of a supercell, which contains many diffractive features; apodized arrays of diffractive features where the periodicity and/or shape of the diffractive features is varied throughout at least a portion thereof; and arrays of diffractive features with domains, where the spacing, size, and depth or height of the diffractive features is locally uniform within a domain but varies from domain to domain. Other geometries and arrangements are also possible.

The array of diffractive features 220 has a two-dimensional periodicity (the directions of periodicity are not necessarily orthogonal), however, other diffractive optical elements can also be used with respect to one or three dimensional arrays of diffractive features (periodic or not)

Inset 230 illustrates another embodiment of the invention where the diffractive optical element is a diffraction grating on the surface of a diamond facet 210. Diffraction gratings similar to the one illustrated in inset 230 can be patterned onto all of the facets 210 of a cut gemstone or any subset of facets. The diffraction grating 230 can be oriented at any angle and can serve as a transmission grating or a reflection grating, depending upon the angle at which light is incident upon it. In some embodiments, the grating 230 can be etched into the diamond surface. In other embodiments, the grating 230 may comprise material, metal (e.g. gold) strips for instance, that is deposited onto the diamond surface 210. Any number of diffraction gratings can be patterned on the diamond surfaces or inside the crystalline structure.

A wide range of diffractive optical elements are possible. For example, although the diffractive features may be formed by topographical features, in other embodiments the diffractive features may be formed from variations in refractive index. For example, in some embodiments, the plurality of grooves or indentations forming the diffraction grating or lattice may be filled with another material with a different diffractive index than the diamond. The diffractive optical element may also comprise a hologram. Both surface and volume holograms may be used in a similar manner as described above.

Figure 4A:
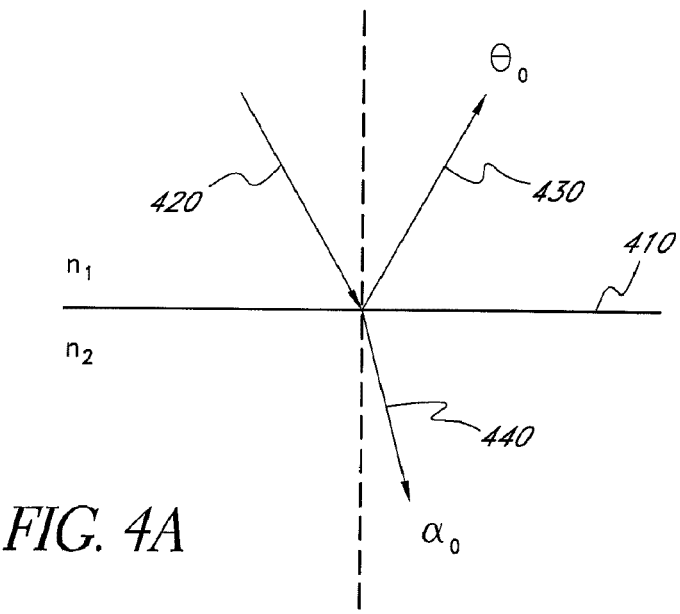
FIG. 4A is a schematic representation of a ray of light incident upon a diamond-to-air interface.

Diffraction gratings are well-understood but will be briefly reviewed in this disclosure. FIG. 4A shows an abstract representation of a diamond-to-air interface 410. It should be understood that similar principles will also apply to other gemstones, natural or synthetic, and even to reflection gratings that are patterned onto metals and other non-dielectric materials. In FIG. 4A, the side of the interface 410 with refractive index $n_2$ represents diamond, while the side of the interface with refractive index $n_1$ represents air. A ray of light 420 incident upon the interface at an angle less than the critical angle will be partially reflected as ray 430, $\theta_0$, and partially transmitted as ray 440, $\alpha_0$. The angle of reflectance will be equal to the angle of incidence, while the transmission angle is governed by Snell's Law of refraction. Rays of light within the diamond (not shown) that are incident upon the interface 410 (from the diamond side) at angles greater than the critical angle will be totally reflected.

The natural fire of a diamond results from the fact that the refractive index of diamond is wavelength-dependent, meaning that light rays of different wavelengths that are refracted at a diamond-air interface will propagate at slightly different angles. This dispersion effect also occurs when light enters the diamond. Accordingly, light of different wavelengths propagates along different optical paths at different angles. Thus, as a result of dispersion, component colors of white light are separated and are visible from different angles of view, resulting in fire.

Figure 4B:
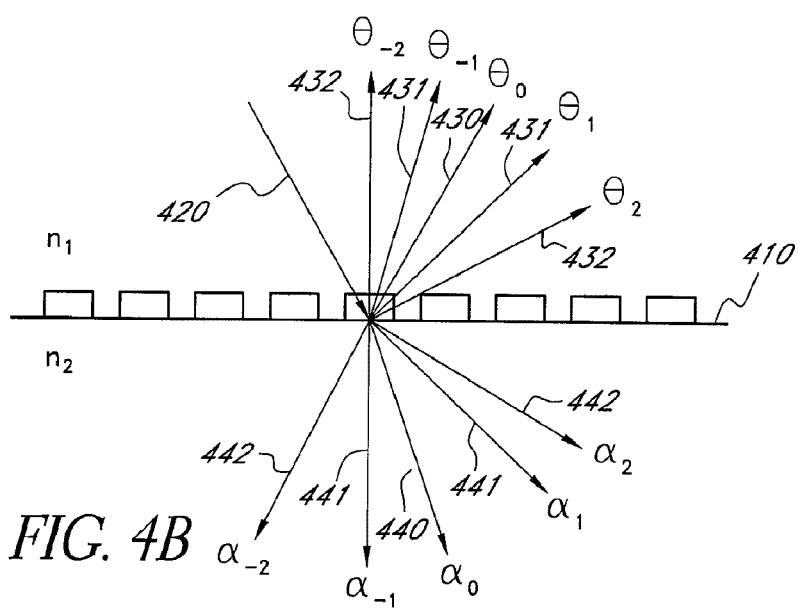
FIG. 4B is a schematic representation of a ray of light incident upon a diffraction grating at a diamond-to-air interface.

A diffraction grating can be used to greatly increase the separation of different wavelengths thereby enhancing fire, as explained with respect to FIG. 4B. FIG. 4B illustrates the effect of a diffraction grating at the interface 410. The same incident ray 420 results in many different reflected rays, $\theta_n$, and transmitted rays, $\alpha_n$. Each of these reflected and transmitted rays represent a diffractive order of the grating. The reflected and diffracted rays that occur at the same angles as those that would exist in the absence of the grating are called the $0^{th}$ order rays. FIG. 4B also illustrates the ±1 and ±2 orders, as indicated by the subscripts on the reflected and diffracted rays.

Figure 5:
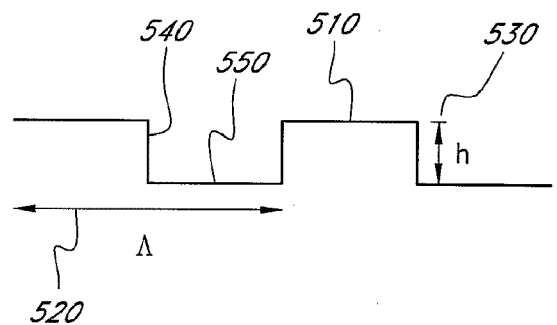
FIG. 5 is a cross-sectional view of a diffraction grating.

A cross-sectional view of one embodiment of the diffraction grating 230 having a surface profile 510 in FIG. 5. The grating profile 510 of this embodiment is a square wave with a period 520, Λ, and a peak-to-peak amplitude 530, h. Diffraction gratings with differently shaped profiles can also be used, however, depending upon the particular fire effect that is desired, as will be described below. For example, the grating 230 could have a sinusoidal or saw-tooth profile, to name only two examples.

The diffraction grating illustrated in FIG. 5 is a spatial phase modulator. In particular, it is a surface relief grating and operates by spatially modulating the phase of incident light waves. The diffractive features of the illustrated grating comprise etches into the surface of a gemstone which operate by locally modifying (e.g., shifting) the phase of light propagating through, or incident upon, them. The depth of the various etches illustrated in FIG. 5 is substantially uniform, resulting in a binary spatial phase modulator. In other embodiments, the plurality of etches could have a variable depth. In still other embodiments, spatial phase modulation could be achieved by variations in refractive index. Many other types of diffraction gratings can be used as well. For example, these can include gratings that spatially modulate the amplitude of incident light, whether by selective reflection or absorption, etc. Gratings can also be designed and used in various embodiments which combine more than one of these effects. The equation governing the behavior of diffraction gratings in general is referred to as the grating equation:

$$n_2 \sin(\alpha_i) = n_1 \sin(\theta) + i\frac{\lambda}{\Lambda}, \quad \text{(Equation 2)}$$

where Λ is the period of the grating, λ is the wavelength of incident light, and i is an integer representing the diffractive order. When i is non-zero, as is the case for the higher diffractive orders, the angle of diffraction is strongly dependent upon wavelength, which can result in a fire effect that is much stronger than the natural fire of a diamond. Furthermore, the dispersive fiery effect of a grating is generally stronger for smaller grating periods because the non-zero orders have a greater angular separation from the $0^{th}$ order.

The angles of each of the diffractive orders of the grating are determined by the period of the grating or the distance between like portions of the grating features. The period of the grating or distance between like portions of the grating features can be referred to as its structure factor. However, neither the structure factor of a grating, nor the diffraction grating equation above describes the relative intensities of light rays in each of the diffractive orders. The relative intensities are dependent upon the shape of the profile of the grating and can be referred to as the form factor of the grating. The method of calculation of the relative intensities of diffracted rays from the form factor of a grating is approximately related to the Fourier transform of the grating profile and is within the ability of one of ordinary skill in the art.

While the form and structure factors used in certain embodiments of the invention will be described in this disclosure, it should be understood that a wide variety of different combinations of form and structure factors could be used. Different combinations of form and structure factors can be used to create different optical effects that will result in diamonds with different appearances.

Figure 6A:
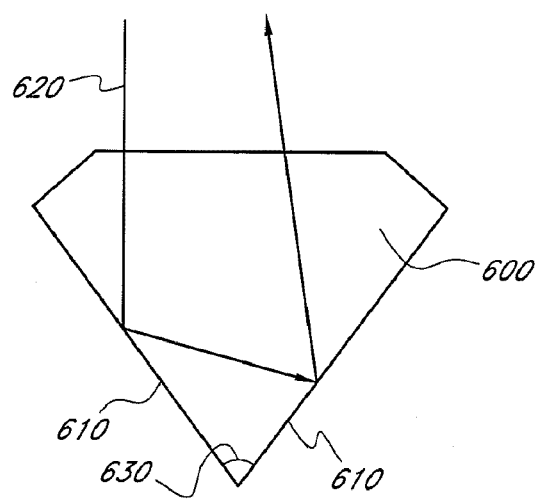
FIG. 6A is a schematic representation of the optical path of a ray of light through a diamond.
Figure 6B:
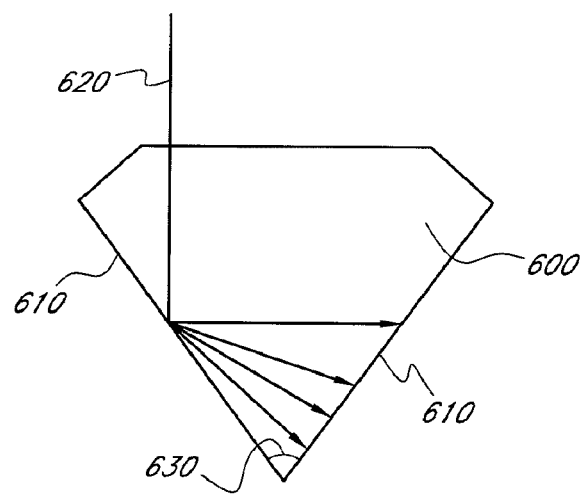
FIG. 6B is a schematic representation of the optical path of a ray of light through a diamond having a diffractive optical element patterned thereon.

FIGS. 6A and 6B, respectively, illustrate a typical light ray path through a diamond with and without the presence of diffraction gratings on surfaces of the diamond. FIG. 6A shows and incident ray 620 which enters a diamond 600 through the table portion of the crown. The ray is internally reflected within the diamond at the pavilion facets 610 and exits the diamond, again through the table, the pavilion behaving similarly to a corner reflector. FIG. 6B illustrates the path of a similar incident ray 620, which enters the diamond 600 through the table portion of the crown. However, in this case a diffraction grating has been patterned on the first pavilion facet 610 along the ray's path. The diffraction grating separates the incident ray 620 into a number of reflected rays, $\theta_n$, each with a different direction of propagation. The reflected rays travel along their new angular path to be reflected or transmitted at some other point along the diamond's surface.

In some embodiments of the invention, there are points of complexity which can arise with the introduction of diffraction gratings on the surface of a diamond, or other gemstone. First, the presence of a diffraction grating along a pavilion facet 610 can result in imperfect total internal reflection, resulting in some light escaping the diamond which would otherwise be totally internally reflected. This can result in loss of brilliance. In certain embodiments, this may be tolerable, while in others, the diffraction gratings can be designed to reduce or minimize this loss.

Second, when the incident light ray 620 is split into a number of diffractive orders at the first pavilion facet, not all of these orders will strike the second pavilion facet at an angle such that they can be reflected back through the crown. In general, it may not be possible to design the culet angle 630 such that each of the diffractive orders is reflected back through the crown of the diamond, or even reflected at all, at the second pavilion facet along the optical path of incident ray 620. This, too, can result in a loss of brilliance.

Finally, the fact that light rays may be steered by more than one diffraction grating on or within the diamond creates complexity. This may result, for example, in some of the higher-order rays from a first diffraction grating being steered back into the $0^{th}$ order by a second diffraction grating, with little or no resulting fire enhancement. Proper design of the diffraction gratings 230 can be used to address each of these complexities.

One preferred embodiment of the invention which addresses each of these points of complexity is illustrated in the cross-section 510, or profile shown in FIG. 5 and discussed above. In certain embodiments, the grating 510 is patterned onto one or more of the pavilion facets 610 of a round brilliant cut diamond. As shown, the grating of FIG. 5 comprises a series of trenches, whose sidewalls 540 can be relatively steep so that the sidewalls account for only a small fraction of the footprint of each trench. However, the steepness of the sidewalls is not critical and the sidewalls may be on average angled between approximately 0° and 60° with respect to the bottom of the trench (where 0° is taken to be perfectly perpendicular to the trench bottom). Furthermore, in certain preferred embodiments, the trenches are relatively shallow such that the aspect ratio of the height of a trench 530 to its width 550 is relatively small. In these embodiments, the aspect ratio of the trench height 530 to its width 550 may be approximately in the range of 0.0005 to 0.25. In more preferred embodiments, the aspect ratio can be in the range of 0.0025 to 0.1. Other ranges are also possible. The bottom 550 of each trench can be substantially optically flat and parallel to the diamond surface upon which the grating is patterned. The grating profile of FIG. 5 will occasionally be referred to as a square wave with the understanding that the profile of the grating may not be perfectly "square." In other words, the trench walls 540 may not be perpendicular to the trench floors 550 and the trench walls 540 and trench floors 550 may not be perfectly planar. In some embodiments, the edges may be rounded.

The duty cycle of the square wave profile 510 shown in FIG. 5 is approximately 50% and the period 520, $\Lambda$, is such that the grating is somewhat higher order for visible light, meaning that the periodicity is many times the wavelength range of visible light. This higher order design has benefits, despite the fact that the dispersive effects of diffraction gratings generally increase with smaller periodicity, which will be explained below. In some embodiments, the period is approximately in the range of 1-100 microns. In other preferred embodiments, the period can be approximately in the range of 2-50 microns. In some preferred embodiments, the period can be in the range of 4-20 microns. In one preferred embodiment, the period 520, $\Lambda$, is approximately 10 microns. This structure factor results in adequate angular separation between the $0^{th}$ order and the ±1 diffractive orders. The angular separation between diffractive orders will, in general, also be dependent upon the angle of incidence of light upon the grating. This can in turn depend upon the geometry of the gemstone being used as well as the particular optical paths through the gemstone of light rays that are of interest in a given design. For example, in a round brilliant cut gemstone, light rays which enter the crown and are reflected back out of the pavilion are particularly of interest in the optical design. In some embodiments, the periodicity of the grating can be chosen such that the angular separation between the $0^{th}$ order and the ±1 diffractive orders for incident rays of interest is less than approximately 15°, though it may also be made greater. In certain preferred embodiments, the angular separation between the $0^{th}$ order and the ±1 diffractive orders is less than approximately 5° for incident rays of interest.

The form factor of the diffraction grating illustrated in FIG. 5 is determined, in part, by the height 530 or depth, h, of the trench walls 540. As previously discussed, the form factor of the grating determines the relative intensity of light in the various diffractive orders. As an analytical tool, it is useful to think of one period of the grating 510 as comprising two parallel mirrors (light incident upon the grating from within the diamond at angles greater than the critical angle will be reflected) offset by the distance h. Light incident upon each of these mirrors will be reflected and will incur an h-dependent phase shift in relation to light reflected by the other mirror. If this phase shift is an integer multiple of $2\pi$, the grating will behave approximately as a single mirror and the majority of light will be reflected into the $0^{th}$ order. If, however, the phase offset is an odd integer multiple of $\pi$, the majority of the incident light power will be reflected into the $\pm 1$ orders. The phase shift (in multiples of $\pi$), m, can be calculated according to the following equation:

$$m = \frac{4\cos(\theta)nh}{\lambda},$$ (Equation 3)

where $\theta$ is the angle of incident light upon the grating, n is the refractive index of the gemstone, h is the trench height 530, and $\lambda$ is the wavelength of incident light. Generally speaking, the grating design of FIG. 5 will result in most of the optical power being reflected into some combination of the $0^{th}$ and $\pm 1$ diffractive orders with a negligible amount of power coupled into higher orders. In certain preferred embodiments, the value of h ranges from approximately 20 to 1000 nm. In some preferred embodiments, the value of h can range from approximately 20 to 600 nm. In one particular preferred embodiment, the value of h is approximately 240 nm. While typical dimensions of a diffraction grating used in one embodiment of the invention (that of FIG. 5) have been given in terms of physical sizes, those skilled in the art will recognize that the dimensions could also be specified in terms of optical length, or physical distance of propagation of light multiplied by the refractive index of the medium of propagation. In fact, if a different medium of propagation were selected, the grating dimensions disclosed in this specification may need to be altered in order to maintain similar ranges of optical lengths which would result in similar optical behavior. This conversion is within the skill of one having ordinary skill in the art.

This diffraction grating design addresses the above-described complexities. Due to the relatively small aspect ratio of trench height 530 to trench width 550, a large percentage of light incident upon the grating strikes the tops and bottoms 550 of the trenches, rather than the sidewalls 540, and is totally internally reflected, rather than escaping from the diamond. This helps to maintain the natural brilliance of the diamond cut. The difficulty in adequately reflecting the various diffractive orders, with their diverging angular paths, off the pavilion facets 610 and back through the crown is lessened due to the fact that the form factor of the grating (e.g., the shape of diffractive features) is such that the grating couples most of the light incident upon the grating into the $0^{th}$ and $\pm 1$ orders. The structure factor of the grating (e.g., the period) is such that the grating causes the angular separation between the $0^{th}$ and $\pm 1$ diffractive orders to be less than approximately 15°, allowing much of the light coupled into each of these orders to be reflected back through the crown much as it would in the absence of the grating on a pavilion facet 610.

Finally, the culet angle 630 can be chosen to reduce or minimize the impact of subsequent steering of light rays by reflection off of a second diffraction grating in an optical path similar to that illustrated by ray 620. This is due to variation in the phase offset as the angle of incidence upon the grating varies (See, e.g., Equation 3 which is dependent upon $\theta$ as well as h). In other words, for the case of a round brilliant cut gemstone, a ray of light which enters the table portion 110 of the crown 130 approximately normal to the table surface will strike a first pavilion facet at an angle that is dependent upon the culet angle 530. The angle of incidence as well as the trench height 530, h, of the grating will determine the phase offset according to Equation 3. The angle at which subsequent diffracted rays of light strike a second pavilion facet, and hence the phase offset at that facet according to Equation 3, is also dependent upon the culet angle 530. The culet angle 630 can be chosen so that the phase offset for light incident upon a first diffraction grating along ray path 620 is approximately an odd integer multiple of $\pi$, resulting in strong coupling into the $\pm 1$ diffractive orders, whereas the phase offset caused by a second diffraction grating on an opposing pavilion facet along optical path 620 is approximately an integer multiple of $2\pi$. In this way, the second grating behaves primarily as a mirror without substantially upsetting the diffractive order coupling caused by the first grating along the optical path 620. In certain preferred embodiments, the angle of a corner reflector formed by two or more facets, such as the culet angle, is approximately between the range of 60 and 120 degrees.

As discussed, the diffraction grating 510 of certain preferred embodiments of the invention has a relatively large periodicity (several times the wavelength range of visible light) in order to lessen the angular separation between the $0^{th}$ and the $\pm 1$ orders, thereby allowing for reflection of each of these diffractive orders back through the crown. Furthermore, the form factor (e.g., shape of the diffractive features) of the described grating is such that the grating couples most of the optical power incident upon the grating into the $0^{th}$ and $\pm 1$ orders, rather than higher orders. Each of these characteristics tends to lessen the dispersive effects of the grating since dispersion is greater for smaller grating periodicities and higher diffractive orders. (Other designs according to the invention can be made to take advantage of shorter grating periods and higher diffractive orders to achieve desirable optical effects in gemstones). However, in this design a significant contribution of the enhancement of the fire of the gemstone is due to the fact that across the visible spectrum different proportions of light are coupled into the $0^{th}$ and $\pm 1$ diffractive orders for each wavelength. This is related to the fact that the form factor of the grating will be slightly different for each wavelength of visible light due to the difference in the optical dimensions of the grating at various wavelengths. As a result, the distribution of light into the different orders may vary with wavelength In other words, in a preferred embodiment, the enhanced fire of a gemstone is caused principally by the form factor of a diffraction grating, which may be different for different wavelengths and may be used to control the distribution of different color light in the different orders, while the structure factor is utilized to control the optical paths of diffracted rays (in this case, maintaining brilliance by ensuring that $\pm 1$ diffractive orders are still back reflected through the crown of the gemstone). In other embodiments, the structure and form factors of a diffraction grating could be used in different ways to enhance the optical characteristics of a gemstone.

Figure 7A:
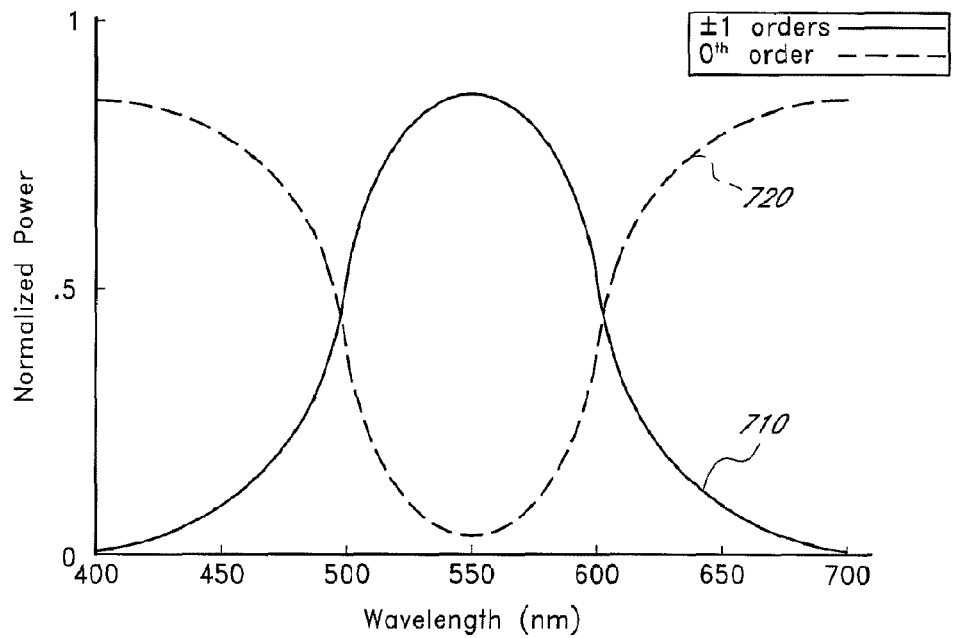
FIG. 7A is a plot of the fraction of light, as function of wavelength, coupled into certain diffractive orders of a diffraction grating according to one embodiment of the invention.

The grating of FIG. 5 can be designed or optimized in a number of ways to achieve a wide variety of optical characteristics. For example, the grating of FIG. 5 can be configured (for example, the trench height can be selected) so that a majority of green light is coupled into the $\pm 1$ diffractive orders, while a majority of red and blue light remain in the $0^{th}$ order. This situation is illustrated in FIG. 7A which shows the proportion of incident light reflected in the $0^{th}$ and $\pm 1$ diffractive orders as a function of wavelength for a beam of white light incident upon the diffraction grating of FIG. 5. In this case, the grating has a trench height or depth 530, $h$, equal to 240 nm. Using Equation 2, and assuming a 90° culet angle 530 such that light normally incident upon the table portion of the crown 110 would strike a diffraction grating located on a pavilion facet 610 at $\theta$=45°, this trench height results in a value of m=3 (a phase shift of $3\pi$) at the green wavelength of $\lambda$=550 nm. The results in strong coupling into the ±1 orders as the majority of the incident light power will be reflected into the ±1 orders if the phase offset is an integer multiple of $\pi$ as described above. Using the same equation it can be seen that m=2 in the red regions of the spectrum and m=4 in the blue regions of the visible spectrum. The result is low coupling into the ±1 orders as the grating will behave approximately as a single mirror and the majority of light will be reflected into the $0^{th}$ order if if this phase shift is an integer multiple of $2\pi$. Curve 710 represents the fraction of light across the visible spectrum that is coupled into the ±1 orders. Note the peak in curve 710 that occurs in the midrange wavelengths of the visible spectrum which roughly correspond to the color green. Curve 720 represents the fraction of light across the visible spectrum which remains in the $0^{th}$ order. Note the peaks in curve 720 which occur near the longer red wavelengths and the shorter blue wavelengths of the visible spectrum. This design would result in a diamond with enhanced green and purple fire.

Figure 7B:
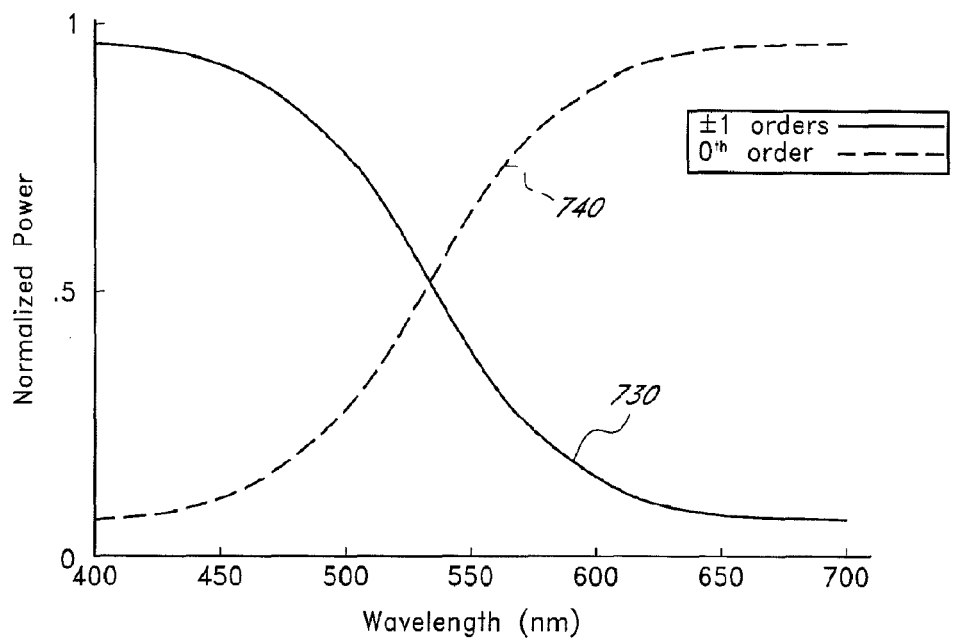
FIG. 7B is a plot of the fraction of light, as a function of wavelength, coupled into certain diffractive orders of a diffraction grating according to another embodiment of the invention.

In another variation, the grating of FIG. 5 could be designed so that a majority of blue light is directed into the ±1 orders, while a majority of red light remains within the $0^{th}$ order, as illustrated by curves 730 and 740, respectively of FIG. 7B. In this case, the trench height or depth 530, $h$, is equal to 186 nm. This design would result in a diamond with enhanced red and blue fire. Accordingly, by varying the trench height 530, $h$, of the grating 510, a broader range of colorful fire effects can be achieved in a gemstone. The dimensions of the grating illustrated in FIG. 5 can be varied to accommodate a variety of tastes.

In still other variations of the grating shown in FIG. 5, the duty cycle could be changed from approximately 50% to other percentages. For example, a duty cycle of approximately 30% or approximately 70% would result in an appreciable amount of coupling of light into the $0^{th}$ order not only when m is an even integer but also when m is an odd integer. This may result in a softer fiery effect. The trench height 530, $h$, can also be varied substantially. For example, for relatively small values of h, the value of m may be less than 1 for all visible wavelengths of light. In this case, the coupling into diffractive orders other than the $0^{th}$ order may never reach full strength. Furthermore, for relatively small values of h there will be less wavelength variation in the effects of the grating, resulting in a more understated enhancement of fire. In summary, with respect to the specific grating illustrated in FIG. 5, three dimensions, for example, can be varied to achieve a variety of optical effects: the trench height 530 can be varied to control color dominances of the fire; period can be varied to control angular steering of diffracted beams; and duty cycle can be varied to control the strength of the enhanced fire as well as coupling into higher diffractive orders.

It should be understood that the diffraction grating design of FIG. 5, along with the several described variations, represents only a single embodiment of the invention. This embodiment is intended to illustrate how certain complexities that may arise with the introduction of diffractive optical elements to the surfaces of some types of gem cuts could be addressed. A myriad of other designs (i.e. diffraction gratings of different shapes and dimensions as well as other arrays of diffractive features) are not only possible but useful to practicing the invention with gemstones of various types, cuts, quality, and sizes in order to achieve a variety of desired optical characteristics. Other designs can be developed with the aid of available method of optical design, including but not limited to analytical methods, finite difference time-domain (FDTD), and finite element methods (FEM).

Modified ray-tracing can also be used as an optical design methodology in certain preferred embodiments of the invention. Ray-tracing algorithms are based on a geometric optical approximation of light propagation and have the benefit that they can be much less computationally intensive than a full simulation of Maxwell's equations such as might be performed using FDTD or FEM. Since the light under which a diamond is typically viewed is polychromatic and has a short coherence length, ray-tracing can be used to quickly model the optical properties of a gemstone with an acceptable degree of accuracy. Ray-tracing algorithms typically catalog the surface properties of the object being simulated in terms of angular dependence of reflectivity and transmission, diffusivity of the surface, etc. and then simulate the paths of a number of light rays based on known laws of reflection, refraction, and absorption. However, since ray-tracing entails a geometric optical approximation of Maxwell's equations, it does not typically account for the effects of diffraction.

However, the increased fire of gemstones that is made possible with the diffractive optical elements described herein depends upon diffractive effects and should be included in the simulation. This can be done by augmenting the ray-tracing algorithm with diffraction algorithms that simulate the diffraction of light from, for example, a diffractive optical element such as disclosed herein. The diffraction of the light can be based on specifications that might include the location of diffractive optical elements on the gemstone, their angular efficiency dependence, and the angles of diffractive orders, as well as their relative intensities, that are caused by the diffractive optical elements. With this information, the ray-tracing algorithm can be modified to simulate the additional light rays that result whenever any given simulated ray is incident upon a diffractive optical element. These properties of the diffractive optical elements may be obtained from a simulation of Maxwell's equations, e.g. FDTD, or from analytical descriptions of the grating. They may be calculated directly by the algorithm, or may be included in a database, entered by a user, etc.

For the diffraction grating illustrated in FIG. 5, and others, the ray-tracing algorithm itself can efficiently calculate the effects of the grating for inclusion in the simulation. The angles of propagation of diffracted rays can be calculated by the algorithm according to Equation 2, so that the algorithm may only need to store the form factor of diffractive features (e.g. in the form of the scattering efficiency of the individual diffractive features). In the case of some periodic spatial phase modulators, including the diffraction grating of FIG. 5, the relative intensities of the various diffractive orders can also be obtained directly by closed form analytical expressions. For example, for the diffraction grating of FIG. 5, where the duty cycle of the grating is approximately 50%, the power reflected in the $0^{th}$ order is approximately given by $\cos(\pi m/2)^2$, where m is given by Equation 3. The total power reflected in the other orders is approximately given by $\sin(\pi m/2)^2$. The fraction of power coupled into a specific higher diffractive order can be obtained from the square magnitude of the Fourier transform of a function g, where g equals −1 in the trough region of the grating and +1 in the unetched, or peak, region of the grating. This method can be adapted and used for a variety diffractive optical elements, paving the way for more computationally efficient simulations of these diffractive optical elements.

When simulating the appearance of a cut gemstone with a convex geometry, the ray-tracing algorithm can be further adapted to accelerate the ray-tracing algorithm. One of the calculation-intensive steps in ray tracing is collision detection, which includes verifying which objects intersect a given ray and in what order. If a gemstone has a convex geometry and can be described by planar facets, this information can be used to simplify the collision detection portion of the ray-tracing algorithm. In these cases, collision detection can be performed by computing, for each facet, the distances between a point within the gem along a ray path and the (infinite) plane in which each facet is contained. This can be done using basic analytical geometry. The facet corresponding to the smallest distance is the facet that actually intersects the ray. For rays escaping the gemstone, the problem is trivial, as those rays cannot intersect with the gemstone again due to its convex geometry. One benefit of this method of collision detection is that it does not require triangulation of the gemstone surfaces, though this still may be beneficial in certain circumstances.

In many cases, the diffractive optical element(s) used according to various embodiments can be designed or optimized by software that includes ray-tracing and simulation of the diffraction of light from the diffractive optical element(s). In this way, modified ray-tracing algorithms, as described herein, can not only simulate the optical characteristics of a "macroscopic" cut of the diamond, but also the appearance that a gemstone will have after being patterned with one or more microscopic diffractive optical elements.

In one embodiment, simulation software that uses, for example, a ray-tracing algorithm, as described above, could be used in conjunction with machine vision techniques to analyze rough hewn gemstones to determine a macroscopic cut (e.g. an optimal macroscopic cut) for the gemstone, whether in terms of weight or brilliance any other desired characteristic. For example, the machine vision system could include a processor and a detector such as a camera to image rough hewn gemstones and determine their dimensions as well as identify the presence of defects such as inclusions. The machine vision system could also comprise a laser mapping system, which could include one or more lasers and one or more detectors to track gemstone position and/or map the shape and features of a gemstone. With this information, the rough hewn gemstone could be analyzed, and a cut determined which emphasizes brilliance, carat weight, or some other property. The simulation software could then be used to determine whether a diffractive optical element should be patterned on the resulting cut gemstone and, if so, the location(s) of diffractive optical elements to achieve a desired appearance. In certain embodiments, a collection of rough gemstones could be sorted to provide the appropriate cut and diffractive optical element(s). In other embodiments, cut diamonds can be processed, for example, using machine vision and/or the simulation software described herein to determine which diamonds should receive diffractive optical elements, where such elements should be located, and/or the specifications for the diffractive optical element (e.g., shape, size, etc.) In other embodiments, customers could be given the option of selecting a pre-cut gemstone and then having the stone analyzed and simulated, whether in person or over the internet, with the described ray-tracing algorithm so that the customer can choose, for example, diffractive optical element types and/or positions which result in an appearance that best suits his or her tastes. The customer's chosen gemstone could then be patterned with his or her selected configuration of diffractive optical elements, as described below. This simulation program may be provided by jewelers or jewelry retail stores or other outfits that may charge the customer for the diamond or for the service of providing the diffractive optical elements on the diamond or even cutting a diamond and providing the diffractive optical element. Other arrangements are possible.

In certain preferred embodiments of the invention, the above-described optical methodologies can be used to create gem designs, entailing both macroscopic cuts and facets, as well as microscopic diffractive optical elements, that direct as much light as possible, in as many lighting conditions as possible, to the areas around junctions between two or more facets of the gem. The junctions between facets of a gemstone are traditionally the locations where fire and scintillation are strongest because of the variety of angles and orientations at which the joining facets are positioned and the corresponding effect of those angles on light incident upon the junctions. In much the same way, the junctions between facets can also be used to further enhance the fire and scintillation caused by the diffractive optical elements according to the present invention. In other words, when diffractive optical elements are designed to steer light to areas surrounding junctions between two or more facets of a gemstone, the enhanced fire resulting from the diffractive optical elements becomes cumulative with natural fire caused by the refractive prism effect of gemstones (diamonds in particular) in these areas. Furthermore, the fire that is visible at these junctions will appear more similar, yet more intense, to the fire which consumers have come to know and recognize, which may give gemstones that include diffractive optical elements described herein a more "natural" appearance.

II. Fabrication Procedures

Figure 8:
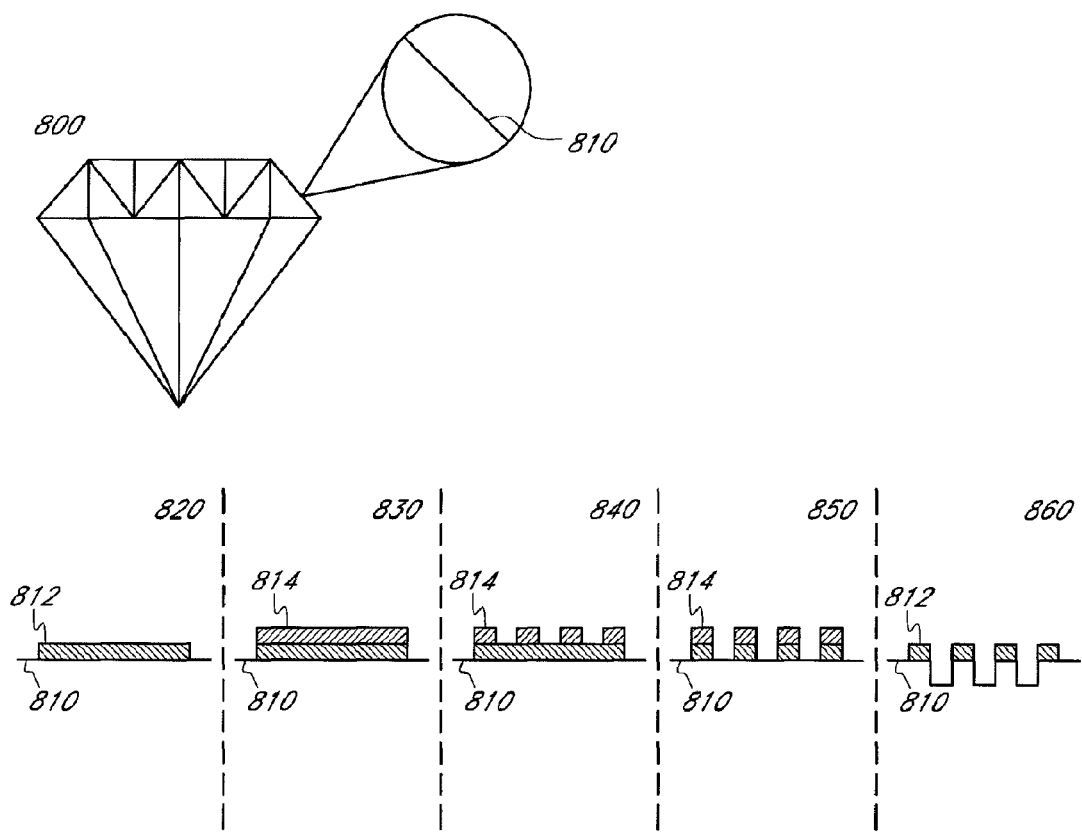
FIG. 8 is a schematic representation of a fabrication procedure for patterning diffractive optical elements onto a surface of a gemstone.

The diffractive optical elements illustrated in the FIG. 2 insets 220 and 230 can be patterned onto gemstones using a variety of techniques, which will be disclosed below. Other methods of manufacture may also be suitable for creating gemstones having patterned diffractive optical elements on the surface or within the gemstone. In particular, several techniques used in the semiconductor industry can be adapted for this purpose. FIG. 8 illustrates a general framework that is shared by several of the methods of manufacture that disclosed herein.

The round brilliant cut diamond 800 shown in FIG. 8 has previously been cut and polished. In certain preferred embodiments, diffractive optical elements can be patterned onto one or more facets of a cut and polished gemstone. In other embodiments, diffractive optical elements can be patterned on any gemstone surface, whether faceted and polished or not. Furthermore, while FIG. 8 illustrates a method of patterning diffractive optical elements on a diamond, any other gemstone can also be used. The inset illustrates a magnified view of one facet 810 of the diamond 800. The facet surface 810 is replicated in each of the frames 820, 830, 840, 850, and 860 in the lower portion of FIG. 8 that illustrate individual processing steps in the fabrication of a diffractive optical element on the facet surface 810. At frame 820, a mask layer 812 is deposited onto the facet surface 810. The mask layer 812 may comprise any suitable material. For example, titanium, aluminum, platinum, chromium, silicon dioxide, and silicon nitride may serve as suitable mask layers. In one preferred embodiment the mask layer 812 comprises a film of gold approximately 100 nm thick. Other thicknesses can also be used.

Next, at frame 830, a resist layer 814 is deposited on the mask layer 812. The precise material used for the resist layer 814 can vary and will depend on the particular fabrication process that is chosen. For example, if an electron beam lithography process is used, the resist layer 814 can be any material that is sensitive to exposure by an electron beam. In one embodiment, polymethylmethacrylate (PMMA) is used as an electron beam-sensitive resist layer. In other manufacturing processes, such as direct laser lithography, projection lithography, various types of interference lithography, and combinations thereof, the resist layer 814 can be any material that is sensitive to exposure by a laser source of choice. Many such materials are known in the semiconductor industry.

Any method capable of depositing a uniform mask layer 812 and a uniform resist layer 814 can be used to perform the processing steps illustrated in frames 820 and 830. In one preferred embodiment, a number of gemstones, which may have already been cut and polished, are provided within a holder. The holder positions the gemstones so that each of the desired facets 810, or other surfaces, can be coated with a mask layer 812 and a resist layer 814 and then exposed simultaneously, or nearly so. The holder may comprise a tray with a number of gemstone compartments. The compartments can be coated with a release agent, such as vacuum grease, and then filled with a putty material. Once the compartments have been filled with the putty, the gemstones may be slightly depressed into the putty. The orientation of the gemstones within the putty can vary depending on the intended location of the diffractive optical elements upon the gemstones. In the case of round brilliant cut gemstones, they may be positioned crown-up, pavilion-up, or in any intermediate orientation. After the gemstones have been positioned in the putty, the entire tray assembly can be pressed against an optical flat, or other planar surface, to ensure that each gemstone is positioned at a uniform height. The putty can then be allowed to cure, locking the gemstones in place.

Once the gemstones are secure, a metal mask layer 812 can be evaporated onto the surfaces of the gemstones. The holder may then be positioned in a spinner and a drop of resist material put on each gemstone, for example with a pipette-type device. The spinner is then rotated at high speeds to spread the drop of resist material into a uniform resist layer 814. Conventional spinners can be used in certain embodiments. However, they may have the disadvantage that gemstones located at different radial distances from the axis of rotation of the spinner can be coated with layers of resist of varying thicknesses due to the difference in centrifugal force at the different radii. The thickness of the resist coating is likely to be inhomogeneous even over the surfaces of a single gemstone, depending upon the flow of resist material over the surfaces of the gemstone under centrifugal forces. For example, resist material on a surface of a gemstone nearer the axis of rotation will be forced outward under centrifugal forces but may be obstructed by the surface of the gemstone itself. Resist material on the far side of the gemstone, in relation to the axis of rotation, will likely see no such obstruction. In other cases, resist on a surface nearer the axis of rotation may flow around the gemstone, and accumulate on surfaces on the far side. These disadvantages can be overcome, in certain preferred embodiments, by using a new type of spinner, as illustrated in FIG. 9A.

Figure 9A:
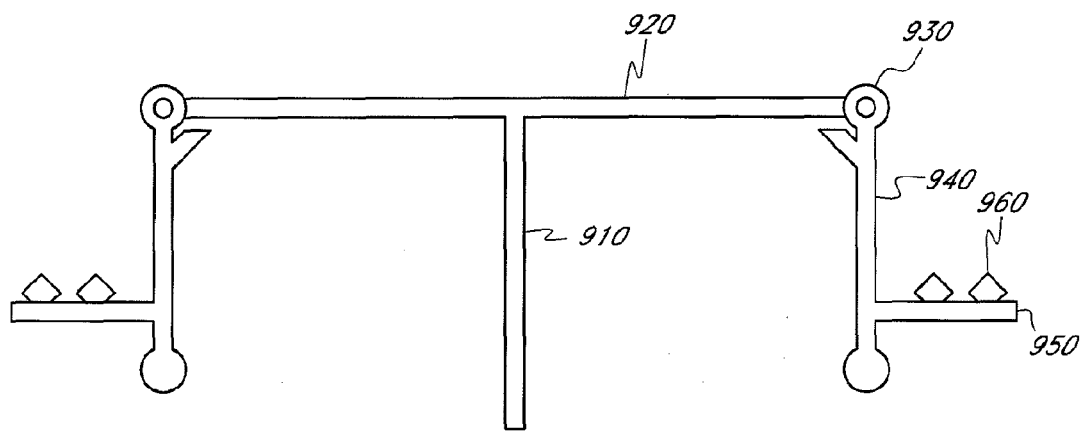
FIG. 9A is a schematic representation of a spinner for use in patterning diffractive optical elements on gemstones or other jewelry.

In certain preferred embodiments, the spinner of FIG. 9A may comprise a central portion 910 from which one or more arms 920 radially extend. The arms can include joints 930 which allow segments 940 of the arms to hang substantially vertically under the force of gravity. The hanging portions of the arms 940 can be adapted to support holders 950 containing one or more gemstones 960. The gemstones 960 can be positioned within the holders so that the surfaces to be patterned with one or more diffractive optical elements are exposed. In some cases, round brilliant cut gemstones will be positioned so that the culet is pointing up. The hanging portions of the arms 940 can hang freely or can be secured with a locking mechanism for stability while drops of resist are applied to the gemstones. In some embodiments of the spinner, a plurality of radially extending arms 920 could be mechanically linked to provide structural support. In other embodiments of the spinner shown in FIG. 9A, the function of the arms 920 could be performed by other structures such as a disk (as seen from above) with hinged portions around the perimeter of the disk. Other geometries are also possible.

Figure 9B:
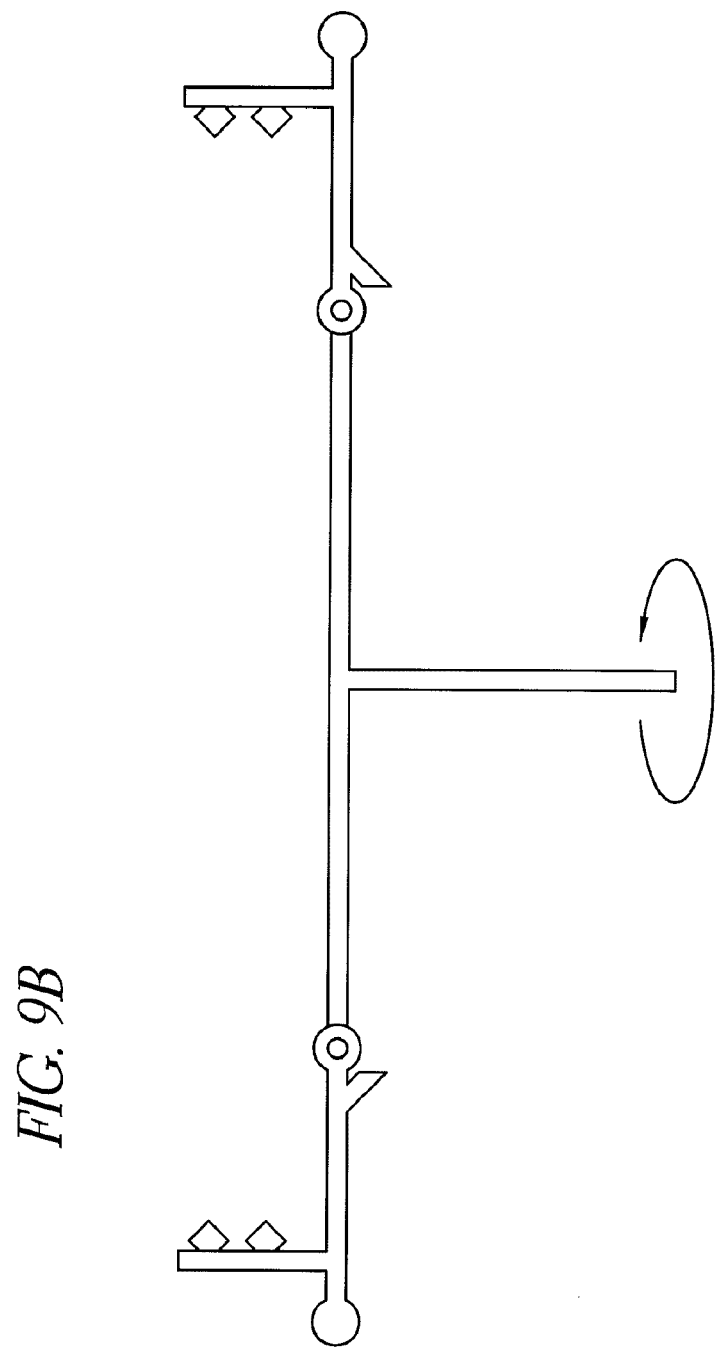
FIG. 9B is a schematic representation of a spinner in an actuated configuration.

Once drops of resist material have been added to the surfaces-to-be-patterned, the spinner begins to rotate. If the center of mass of the hanging portions of the arms together with the diamond holders is lower than the arm joints, centrifugal force will cause the hanging portions of the radial arms to rise and orient the exposed gemstone surfaces more toward the axis of rotation, as illustrated in FIG. 9B. In this orientation, the centrifugal force on each gemstone, and on each surface of individual gemstones, is more balanced, resulting in more uniform resist layer coatings. In embodiments of the described spinner which rely on centrifugal force to re-orient the gemstone holders, weights can be added to the holders and spinner arms as necessary to achieve a desirable center of mass. In other embodiments, actuation mechanisms could be used to re-orient the hanging portions of the arms 940. In some embodiments, the described joints 930 in the radial arms 920 can be omitted such that portions of the arms do not hang vertically and the exposed surfaces of the gemstones always point toward the axis of rotation. However, allowing portions of the arms to hang vertically during application of the resist material may simplify this task since the gemstones will be in an orientation where drops of resist material can be more easily applied.

After the resist layer 814 has dried, it can be exposed and the diffractive optical elements etched into the facet surfaces 810, as described below, after which the gemstones are expelled from the holder compartments.

Once the mask 812 and resist 814 layers have been applied to the facet surface 810, the resist layer can be exposed and developed with an appropriate developing solution. There are a number of options for exposing the resist layer 814, including, but not limited to, electron beam lithography, direct laser lithography, projection lithography, various types of interference lithography, and combinations thereof.

In the case of an electron beam lithography process, exposing the resist layer 814 can be done by selectively scanning or sweeping an electron beam over the facet surface 810 in the pattern of the desired diffractive optical element, whether by moving the electron beam or by moving the gemstone with respect to the electron beam. A scanning electron microscope (SEM) can be used to provide the electron beam. In some embodiments, the feature size of the diffractive optical elements patterned onto the gemstone surfaces 810 can be limited by the spot size of the electron beam. The surface height variation that can be tolerated before the electron beam is out of focus to the extent that resolution is compromised is referred to as the depth of focus, or Rayleigh length. The depth of focus of a conventional SEM is generally about 0.5 mm, but since SEMs are typically used on surfaces with a small amount of height variation, depth of focus usually does not create a problem. However, in the case of using an SEM to pattern diffractive optical elements onto gemstone surfaces, the depth of focus becomes much more critical since the gemstone surface to be patterned can vary in height by several millimeters or possibly even centimeters.

Figure 10:
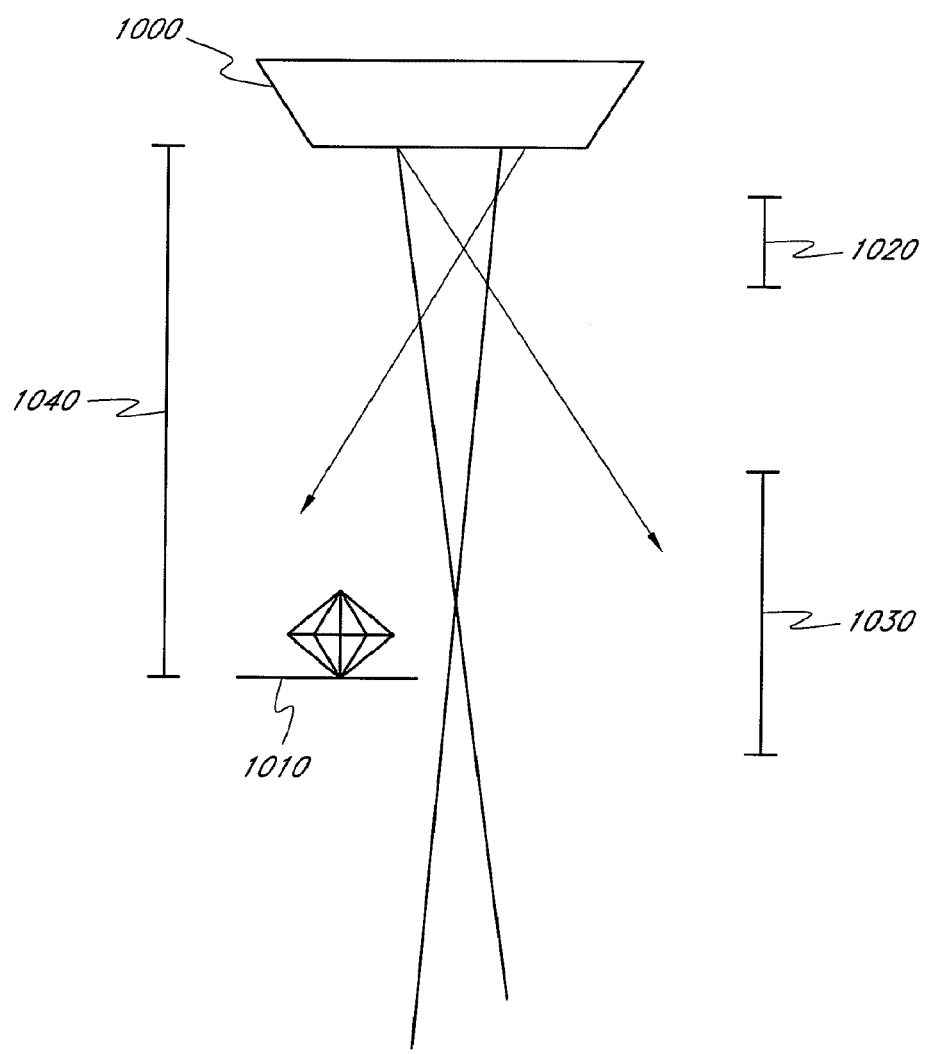
FIG. 10 is a schematic representation of the setup of an electron beam scanning apparatus according to one aspect of the invention.

The problem can be solved by using an SEM in a non-standard configuration where the working distance between the final aperture of the SEM is increased to be much longer than is conventionally used. This arrangement is illustrated in FIG. 10, which shows an electron beam source 1000 separated from a gemstone 1010 by a working distance 1040. By increasing the working distance and appropriately lengthening the focal distance of the electron beam, a much larger depth of focus 1030 is obtained, as compared to the depth of focus 1020 that would result from a shorter working distance and a shorter focal length. Accordingly, in various embodiments the focal length and working distance can be greater than approximately 10 cm, allowing a depth of focus of greater than about 2 mm to be obtained. In more preferred embodiments, the depth of focus can be greater than about 5 mm. In a typical SEM, a 50 nm spot size can still be maintained at a working distance of over 10 cm, which enables electron beam lithography to be conducted with adequate depth of focus to pattern a standard 1-carat diamond.

Figure 11:
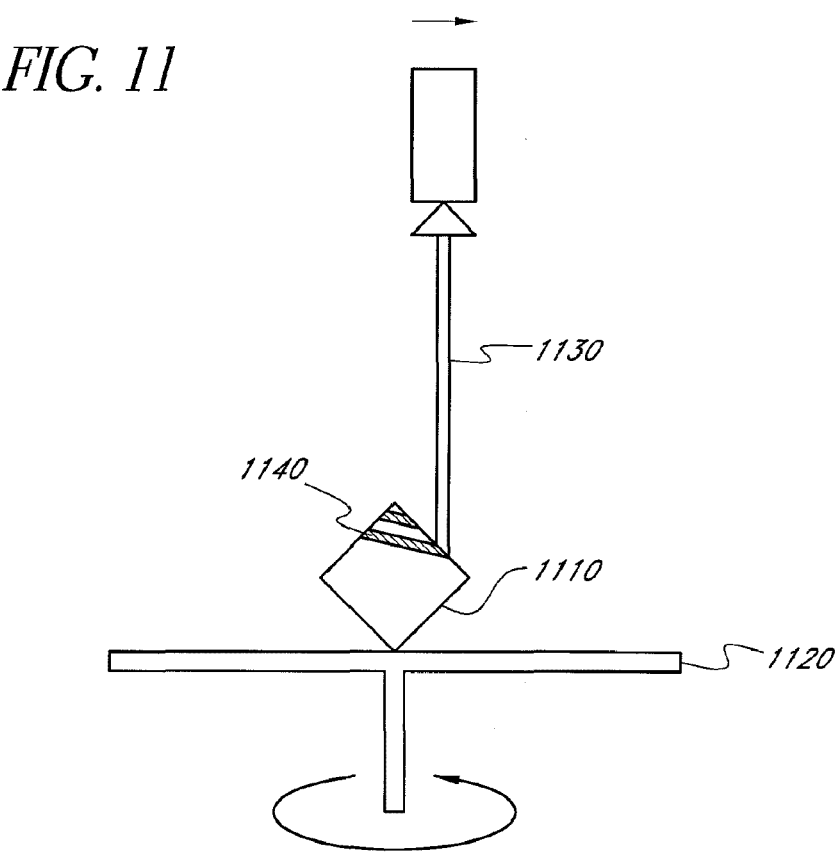
FIG. 11 is a schematic representation of an exemplary method of directly exposing a resist layer with a laser to form diffractive optical elements on gemstones or other jewelry.

The resist layer 814 can also be exposed directly with a focused laser beam. In much the same way as with electron beam lithography, the laser beam is selectively scanned or swept over the gemstone surfaces in the pattern of the diffractive optical element-to-be-formed using a beam steering mechanism. In other embodiments, the use of a beam steering mechanism can be avoided using the scanning strategy illustrated in FIG. 11. A gemstone 1110 can be disposed on a rotating stage 1120. The laser beam 1130 can be focused or de-focused, as necessary, so that its diameter corresponds to the width of a desired diffraction grating trench 1140. The laser beam, or the gemstone, can then be moved in one direction at a constant speed while the gemstone is rotated about an axis that passes through the culet. In one embodiment, the lateral speed of the laser spot relative to the gemstone corresponds to approximately one period of the grating per revolution of the gemstone. This results in a spiral grating on the pavilion of the gemstone without the need for a sophisticated beam steering mechanism. It should be understood, however, that this in other embodiments, the stage 1120 could also be moved vertically, to maintain laser spot size for different heights on the gemstone. The stage 1120 could also be moved translationally in any manner appropriate to expose a resist layer 814.

Figure 12:
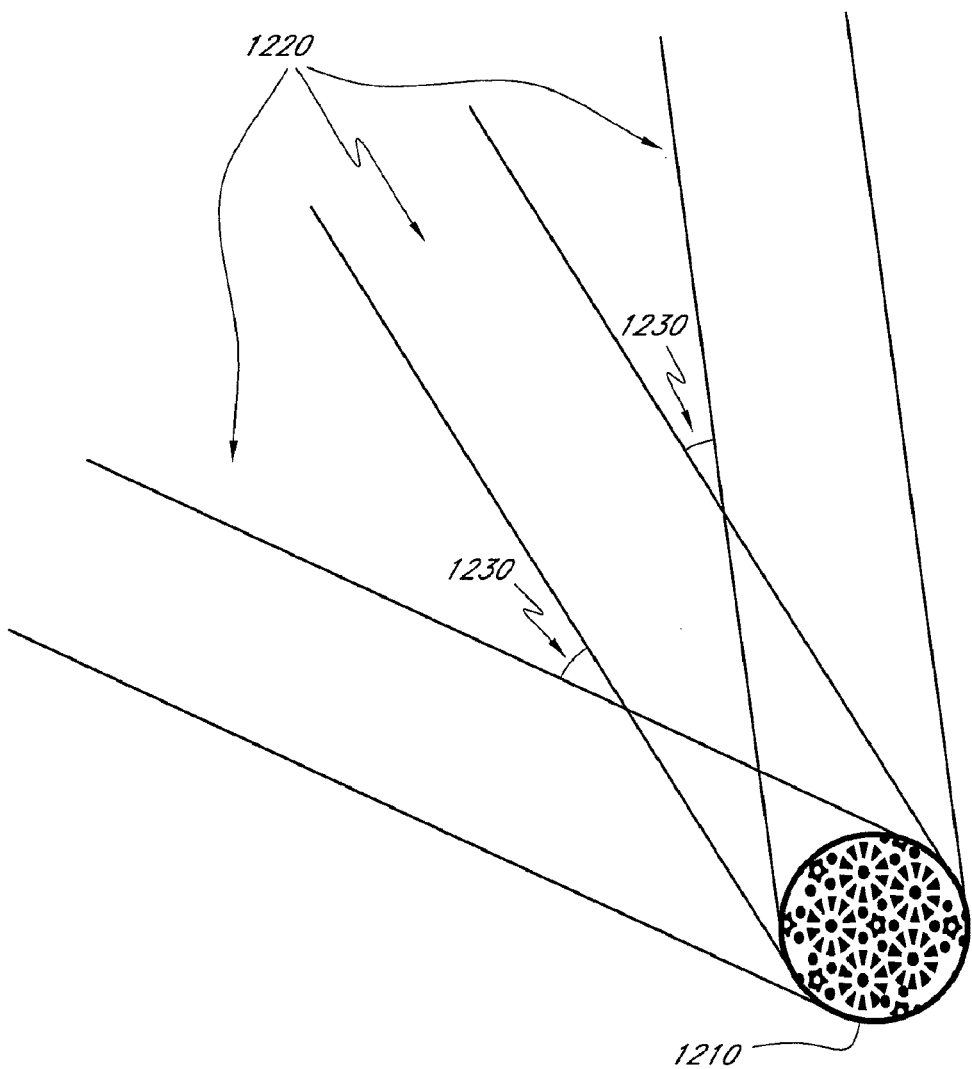
FIG. 12 is a schematic representation of an exemplary method of exposing a resist layer using an interference pattern created by two or more laser beams in order to form diffractive optical elements on gemstones or other jewelry.

In various other embodiments, the resist layer 814 can be exposed by imaging a reticle containing the desired pattern of diffractive features onto gemstone surfaces. Interference lithography, too, can be used to expose the resist layer 814. In this method, an electromagnetic wave or optical interference pattern creates spatial modulation of the intensity of the electromagnetic radiation that selectively exposes the resist layer 814. The interference pattern can be created by interfering two or more lasers (in some cases expanded and collimated), as shown in FIG. 12. FIG. 12 illustrates an interference pattern 1210 formed by interfering multiple laser beams 1220. The characteristic length of the resulting interference pattern can be modified by changing the relative angles 1230 between the laser beams 1220. An interference pattern can also be created by illuminating a hologram or a phase shift mask. A phase shift mask may act as a conventional mask by selectively blocking and transmitting light in a desired pattern. However, a phase shift mask may also comprise a variable thickness plate through which laser light is shined. The variations in thickness of the plate spatially modulate the phase of the laser beam, resulting in interference fringes which can selectively expose the resist layer 814. By modulating both phase and intensity of incident light, a phase shift mask can give greater latitude in tailoring the pattern of a diffractive optical element to be patterned on a gemstone. The phase shift mask can be designed so that the resulting interference pattern matches the desired pattern of the diffractive optical element that is being formed. Phase shift masks may also be useful in reducing depth-of-focus-related problems associated with some forms of projection lithography and can allow for the formation of relatively sharp diffractive features. For example, the phase shift mask can be configured to vary phase and intensity to provide wavefronts of a desired shape and pattern Another method of forming an interference pattern to selectively expose the resist layer 814 comprises using the macrostructure of a gemstone itself to re-direct a coherent beam of light incident upon the gemstone such that the beam interferes with itself to create an interference pattern that selectively exposes a resist layer 814. For example, a laser could be directed onto the crown of a round brilliant cut diamond. The laser beam enters the diamond and, as discussed previously, is reflected off of the pavilion walls back towards the crown. As the re-directed laser beam emerges from the crown of the diamond, it will interfere with itself at the crown as the laser beam directed into the diamond is incident on the crown as described above. This optical interference creates an interference pattern that can develop a resist layer 814 located on the crown. The beam reflected off of a first pavilion facet onto a second pavilion facet can also interfere with light transmitted directly through the crown to the second pavilion facet, thereby exposing a layer of resist located on the second pavilion facet from inside the diamond. In this case, a resist layer lift-off process can be used to transfer the resulting pattern to a mask layer.

In a resist layer lift-off process, a resist layer is deposited on a facet surface before a mask layer (unlike what is shown in FIG. 8). The resist layer can be exposed and developed before a mask layer is deposited on top of it. After a mask layer is deposited, the resist layer can be dissolved, causing the portions of the mask layer on top of the dissolved resist layer to break off. This type of process is particularly advantageous when the resist layer is exposed from within the gemstone, as described, because the resist layer, rather than a mask layer, is in contact with a gemstone facet surface.

Greater flexibility in achieving the desired exposure pattern using the method of internal exposure of a resist layer can result from coating certain facets with reflective layers to prevent light from exiting the gemstone at those facets so that it can be used for contributing to an interference pattern at a subsequent surface along the optical path of light. In other cases, certain facets of the gemstone can be immersed in an index matching fluid so that light does exit the gemstone at those surfaces and does not contribute to an interference pattern at a subsequent surface along the optical path of light within the gemstone.

As an alternative to the methods that have been described for exposing and developing the resist layer 814 to create the desired diffractive optical elements on the facet surface 810, a nano-imprint technique could also be used. This technique entails using a polymer material as a pseudo-resist layer. The pattern for the desired diffractive optical element can be directly stamped into the polymer material using known nano-imprint techniques. The diffractive optical element pattern is then transferred to the mask layer 812 in much the same manner as described below.

Once the resist layer 814 has been exposed and developed as illustrated at frame 840, the mask layer 812 can be etched with the resulting pattern from the resist layer 814. This processing step can be performed with any suitable method. In certain embodiments, the mask layer 812 is etched with an ion milling process. In this way, the pattern from the resist layer 814 is transferred to the mask layer 812, as shown at frame 850. The pattern can then be transferred to the facet surface 810, as illustrated at frame 860. Again, this processing step can be performed with any suitable method. In certain embodiments, this step is performed with a wet etch. In other embodiments, the diffractive optical element pattern is etched into the facet surface 810 using a plasma process known as reactive ion etching process. Various preferred embodiments of this plasma process can use oxygen, CF4, CHF3, or Ag. This process can be particularly advantageous in creating anisotropic etch profiles, i.e. steep trench walls 540. In some embodiments, it may be desirable to use an inductively coupled plasma reactive ion etching (ICP-RIE) process to transfer the diffractive optical element pattern to the facet surface 810. This process results in a plasma with more uniform properties which can be beneficial in obtaining uniform etches over the 3D geometry (e.g. height variations) of the gemstone.

In some cases it may be desirable to follow the reactive ion etching process with an isotropic wet etch to smooth rough features of the diffractive optical element or remove residues resulting from the etching process chemistry such as fluoro carbons. In the case of diamonds, amorphous carbon and graphite residues can also be formed on the gemstone during etching and can also be removed with a wet etch. This can occasionally be important to enhance the quality of the diffractive optical elements and maintain brilliance and transparency of a diamond or other gemstone due to the negative effects of these residues on the optical qualities of a gemstone.

In some embodiments, it may be unnecessary to use separate resist 814 and mask 812 layers. The purpose for having both types of layers is generally due to the fact that many types of resist layers are not resistant enough to a selected etch chemistry used to transfer a diffractive optical element pattern into a gemstone surface; the entire resist layer can be etched away before the pattern is satisfactorily formed in the gemstone surface. To overcome this problem, the pattern is first transferred to a mask layer 812 which is more resistant to the etch chemistry. However, there are certain resist materials which are sufficiently resistant to selected etch chemistries such that separate mask layers are not required. One example is the negative electron beam resist hydrogen silsesquioxane. If an etch chemistry-resistant resist layer 814 is used, then at least two steps of the process illustrated in FIG. 8 can be foregone. First, the mask layer 812 at frame 820 is not required. Second, the process of transferring an etch pattern to a mask layer 812, as shown at frame 850, is not required. Other steps remain substantially as described above.

Finally, once the diffractive optical element pattern has been transferred to the facet surface 810, remaining portions of the mask layer 812 (as seen at frame 860) can be removed. In certain preferred embodiments, this is done with a standard gold etch.

In addition to manufacturing methods that share the general processing framework of FIG. 8, several other fabrication methods can also be used to form diffractive optical elements on the surfaces of gemstones. These can include direct laser ablation of gemstone material with a high power pulsed laser. If this method is used on diamond, which has relatively poor absorption, it may be beneficial to use a layer of material substantially optically absorbing to the laser light to increase the efficiency of the laser ablation process. In certain embodiments, graphite can be used. A layer of graphite can be formed on the diamond and a laser can be used to ablate the graphite layer. The heat from this process will convert a layer of the underlying diamond into graphite, which can then be ablated (e.g., to form the trenches or indentations). This process can be repeated as necessary to form the desired diffractive optical elements on the diamond gem.

Another method of forming diffraction gratings in particular on a gemstone, is to use a specialized grating ruling machine to either etch a gemstone surface directly or to etch a pattern into a pseudo-resist layer of the type used in conjunction with the nano-imprinting technique described above. Such a ruling machine could also be used to pattern a metallic mask layer directly.

Yet another method of forming diffractive optical elements on a gemstone employs using self-organized patterns to create patterned mask layers 812 or resist layers 814. There are many processes which result in self-organized patterns of scales that will suitably diffract visible light according to various embodiments of the invention. Any one of these processes known in the art can be used. Two processes, in particular, which result in self-organized patterns will be described below.

In one embodiment, a self-organized pattern can result from immersion of a gemstone in a colloidal bath. For example, when an object is immersed in a colloidal solution of microscopic particles and then removed from the solution under certain conditions, it is possible to obtain a coating of a layer of particles arranged in a two-dimensional array. In certain preferred embodiments, the layer of particles comprises a mono-layer and the particles are organized in a closely-packed, substantially periodic array. The resulting layer of particles can then serve as a mask layer which can be used to transfer the resulting pattern into a facet surface 810 according to the methods described above. The particles can be of any shape and can form any suitable array, whether periodic or not.

In another embodiment, reflow of a deposited layer is used to create a self-organized pattern. For example, a thin film of material can be deposited onto a gemstone. The thin film can be heated, or otherwise made to liquefy, so that it re-flows. As the material reflows it can form a pattern that is suitable for forming a diffractive optical element. In certain embodiments, the material need not be patterned before reflow; the reflow process itself forms a desired pattern. In other embodiments, the deposited material can be patterned in a suitable manner and then made to reflow. For example, a resist layer could be deposited on a gemstone, exposed, and developed as described above. The resist layer could then be made to reflow, thus modifying the pattern in which the resist layer had been previously exposed. The pattern that results from the reflow process can be modified by altering characteristics of the surface tension between various layers deposited on the gemstone (e.g. mask and resist layers) and/or the surrounding medium (e.g. air).

Several of the fabrication methods which have been discussed benefit from knowing the position of a gemstone being patterned with a high degree of accuracy. The position of a gemstone can be determined and tracked with any suitable technique, one of which is laser mapping. In the case of diamonds, their fluorescence under X-ray illumination could be used to track their position. Accordingly, the diamond could be illuminated so as to fluoresce and the fluorescence could be detected by an optical detector to determine position and orientation. Lastly, machine vision algorithms could be used in conjunction with a camera, a laser mapping system, or other sensing device and processor to track the position and orientation of a gemstone during the fabrication process by identifying recognizable features of the gemstone, such as the culet. One illustrative use of this type of system could be used to center a round brilliant cut gemstone on a rotatable, x-y translatable stage. For example, the gemstone could be placed, with the culet facing up, at any position on the stage. The stage could then be rotated and the machine vision system used to identify whether the gemstone is off-center with respect to the axis of rotation. If the gemstone is off-center, the culet will trace out a circle, easily identifiable by machine vision which can be configured to provide feedback to translate the gemstone in the x and y directions such that the radius of the traced out circle is reduced. By this method, the gemstone can be precisely centered on the stage. Other methods using machine vision algorithms could also be used and applied to other cuts of gemstones.

Figure 13:
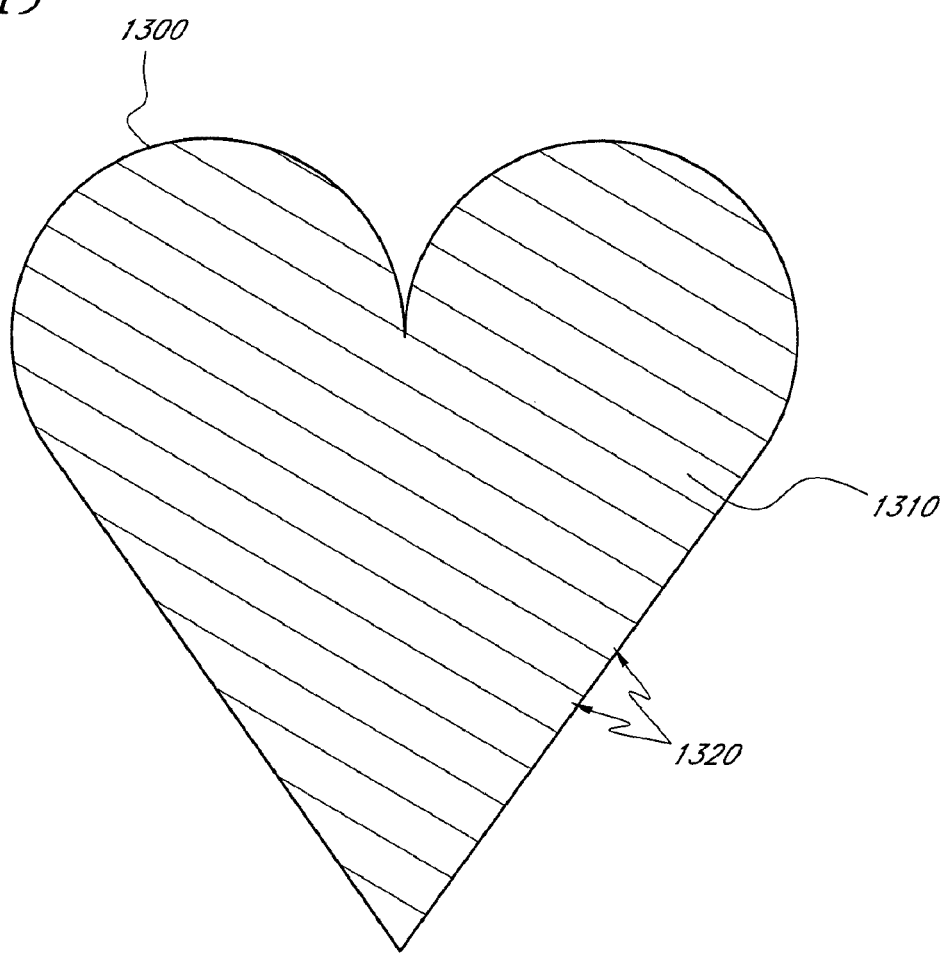
FIG. 13 is a schematic representation of a diffractive optical element formed in the shape of a graphical feature according to one embodiment of the invention.

According to the described fabrication methods, or any other suitable method, diffractive optical elements can be patterned on a gemstone. The diffractive optical elements can be patterned on any gemstone surface or facet, at any orientation, in any pattern, and have any size. In fact, the diffractive optical elements can even be formed in a macroscopic shape (not to be confused with the microscopic individual diffractive features of those elements). This is illustrated in FIG. 13 where a diffraction grating 1310 (here comprising a plurality of linear trenches 1320) is formed in the shape of a graphic (e.g., a heart) 1300 that would be visible on the gemstone to the naked eye. In one embodiment, an outline of a desired diffractive optical element shape can be etched to an etch depth that increases visual contrast so that the design can be more easily seen, though this is not required. The diffractive optical element can then be patterned on the etched surface in the shape of the desired graphic. In this way, a diffractive optical element can literally take the form of any design, logo, symbol, or other graphical feature. The design will appear fiery and can easily catch the eye. This method can be useful for personalization of a gemstone or for branding purposes, etc. It can be used to create graphical features which are visible to the naked eye or are small enough that they remain invisible to the unaided eye, which may be desirable for giving the gem a discreet identification mark.

One advantage of the processed described herein is that the gemstone can be subsequently modified, for example, to provide a new design which may be desired by the consumer to give the gemstone a fresh appearance or to correct a defect. For example, in certain embodiments, the diffractive features will generally be shallow. In many cases, therefore, the diffractive features can be easily polished away with little loss in carat weight. Subsequently, a new diffractive optical element could be patterned on the same gemstone. In this way, a single gemstone can be given a different optical appearance time and time again as desired. Once one or more diffractive optical elements have been patterned on a gemstone, the gemstone can be incorporated into any piece of jewelry in much the same way as is known in the art. Thus, gemstones can be incorporated into rings, earrings, necklaces, bracelets, broaches, pendants, belt buckles, cuff links, etc. Such jewelry may further comprises settings, chains, pins, etc., as is customarily used in such jewelry.

It should be understood that the principles disclosed herein can be applied, in addition to diamonds, to any gemstone or other optically transmissive jewelry. In fact the diffractive optical element can be applied even to opaque portions of jewelry items, in the form of reflection gratings, such as gold, silver, or platinum or other materials.

Preferred embodiments of the inventions have been described in connection with the accompanying drawings. However, a wide variety of variation is possible. Components, and/or elements may be added, removed, or rearranged. Additionally, processing steps may be added, removed, or reordered. The various algorithms that have been described herein can be performed in software, hardware, or a combination of the two. Instructions for performing the algorithms can be embodied by a computer program that is executed by the processor as a series of computer-executable instructions. These instructions or data usable to generate these instructions may reside, for example, in RAM or on a hard drive or optical drive, or on a disc or the instructions may be stored on magnetic tape, electronic read-only memory, or other appropriate data storage device or computer accessible medium that may or may not be dynamically changed or updated. Additionally, some or all the processing can be performed all on the same device, on one or more other devices that communicates with the device, or various other combinations. The processor may also be incorporated in a network and portions of the process may be performed by separate devices in the network.

While certain preferred embodiments have been explicitly described, other embodiments will become apparent to those of ordinary skill in the art of the claimed inventions based on this disclosure. Therefore, the scope of the disclosed inventions is intended to be defined by reference to the claims and not simply with regard to the explicitly described embodiments of the inventions.

What is claimed is:

1. A gemstone comprising:
a body comprising diamond, said body having a crown portion and a pavilion portion; and
a first diffractive optical element disposed on or in said pavilion portion of said body, said first diffractive optical element comprising a plurality of diffractive features spaced with respect to each other to diffract visible light,
wherein said first diffractive optical element is disposed on or in a first facet of said pavilion portion of said body along the optical path of a ray of visible light which enters the crown portion of said body, and further comprising:
a second diffractive optical element disposed on or in a second facet of said pavilion portion of said body along said optical path of said ray of visible light through said body,
wherein said first diffractive optical element separates said ray of visible light into a plurality of angularly separated diffractive orders, and
wherein said second diffractive optical element does not substantially reduce the angular separation between said plurality of angularly separated diffractive orders.

2. A gemstone comprising:
a body comprising diamond, said body having a crown portion and a pavilion portion; and
a first diffractive optical element disposed on or in said pavilion portion of said body, said first diffractive optical element comprising a plurality of diffractive features spaced with respect to each other to diffract visible light,
wherein said first diffractive optical element is disposed on or in a first facet of said pavilion portion of said body along the optical path of a ray of visible light through said body, and further comprising:
a second diffractive optical element disposed on or in a second facet of said body along said optical path of said ray of visible light through said body,
wherein said first diffractive optical element couples said ray of visible light into one or more diffractive orders, and
wherein said second diffractive optical element does not substantially upset the diffractive order coupling caused by said first diffractive optical element.

3. A gemstone comprising:
a body comprising diamond, said body having a crown portion and a pavilion portion; and
a first diffractive optical element disposed on or in said pavilion portion of said body, said first diffractive optical element comprising a plurality of diffractive features spaced with respect to each other to diffract visible light,
wherein said first diffractive optical element comprises a first plurality of diffractive features etched to a first depth in said body, and further comprising a second diffractive optical element that comprises a second plurality of diffractive features etched to a second depth in said body, said second depth being different from said first depth.

4. The gemstone of claim 3, wherein said first and second diffractive optical elements comprise a plurality of grooves, and wherein said first depth causes said first diffractive optical element to couple visible light of a selected wavelength primarily into the ±1 diffractive orders, and wherein said second depth causes said second diffractive optical element to couple visible light of the selected wavelength primarily into the 0th diffractive order.

5. The gemstone of claim 3, wherein said plurality of diffractive features of said first diffractive optical element are etched to a depth in said body in the range of 20 to 1000 nm.

6. A gemstone comprising:
a body comprising diamond, said body having a crown portion and a pavilion portion; and
a first diffractive optical element disposed on or in said pavilion portion of said body, said first diffractive optical element comprising a plurality of diffractive features spaced with respect to each other to diffract visible light,
wherein said first diffractive optical element comprises a first plurality of diffractive features having a first form factor, and further comprising a second diffractive optical element that comprises a second plurality of diffractive features having a second form factor, the second form factor being different than the first form factor.

7. A gemstone comprising:
a body comprising diamond, said body having a crown portion and a pavilion portion; and
a first diffractive optical element disposed on or in said pavilion portion of said body, said first diffractive optical element comprising a plurality of diffractive features spaced with respect to each other to diffract visible light,
wherein said first diffractive optical element comprises a first plurality of diffractive features having a first periodicity, and further comprising a second diffractive optical element that comprises a second plurality of diffractive features having a second periodicity, the second periodicity being different than the first periodicity.

8. The gemstone of claim 7, wherein said first diffractive optical element comprises a diffraction grating.

9. The gemstone of claim 8, wherein the period of said diffraction grating is in the range of 2 to 50 microns.

10. A gemstone comprising:
a body comprising diamond, said body having a crown portion and a pavilion portion; and
a first diffractive optical element disposed on or in said pavilion portion of said body, said first diffractive optical element comprising a plurality of diffractive features spaced with respect to each other to diffract visible light,
wherein said first diffractive optical element comprises a hologram.

11. A gemstone comprising:
a body comprising diamond, said body having a crown portion and a pavilion portion; and
a first diffractive optical element disposed on or in said pavilion portion of said body, said first diffractive optical element comprising a plurality of diffractive features spaced with respect to each other to diffract visible light,
wherein said first diffractive optical element comprises a two-dimensionally periodic or quasi-periodic array of separate diffractive features.

12. The gemstone of claim 11, wherein said plurality of diffractive features of said first diffractive optical element comprise a tiled pattern.

13. A method of altering the fire of a gemstone comprising:
providing a gemstone that comprises diamond, said gemstone having a crown portion and a pavilion portion; and
forming a first diffractive optical element on or in said pavilion portion of said gemstone, said first diffractive optical element comprising a plurality of diffractive features spaced with respect to each other to diffract visible light,
wherein said first diffractive optical element comprises a first plurality of diffractive features etched to a first depth in said gemstone, and wherein the method further comprises forming a second diffractive optical element on or in said gemstone, wherein said second diffractive optical element comprises a second plurality of diffractive features etched to a second depth in said body, said second depth being different from said first depth.

14. The method of claim 13, wherein said first and second diffractive optical elements comprise a plurality of grooves, and wherein said first depth causes said first diffractive optical element to couple visible light of a selected wavelength primarily into the ±1 diffractive orders, and wherein said second depth causes said second diffractive optical element to couple visible light of the selected wavelength primarily into the 0th diffractive order.

15. The method of claim 13, wherein said plurality of diffractive features of said first diffractive optical element are etched to a depth in said body in the range of 20 to 1000 nm.

16. A method of altering the fire of a gemstone comprising:
providing a gemstone that comprises diamond, said gemstone having a crown portion and a pavilion portion; and
forming a first diffractive optical element on or in said pavilion portion of said gemstone, said first diffractive optical element comprising a plurality of diffractive features spaced with respect to each other to diffract visible light,
wherein said first diffractive optical element is formed on or in a first facet of said pavilion portion of said body along the optical path of a ray of visible light which enters the crown portion of said body, and further comprising:
forming a second diffractive optical element on or in a second facet of said pavilion portion of said body along said optical path of said ray of visible light through said body,
wherein said first diffractive optical element separates said ray of visible light into a plurality of angularly separated diffractive orders, and
wherein said second diffractive optical element does not substantially reduce the angular separation between said plurality of angularly separated diffractive orders.

17. A method of altering the fire of a gemstone comprising:
providing a gemstone that comprises diamond, said gemstone having a crown portion and a pavilion portion; and
forming a first diffractive optical element on or in said pavilion portion of said gemstone, said first diffractive optical element comprising a plurality of diffractive features spaced with respect to each other to diffract visible light, wherein said first diffractive optical element is formed on or in a first facet of said pavilion portion of said body along the optical path of a ray of visible light through said body, and further comprising:

forming a second diffractive optical element on or in a second facet of said body along said optical path of said ray of visible light through said body, wherein said first diffractive optical element couples said ray of visible light into one or more diffractive orders, and wherein said second diffractive optical element does not substantially upset the diffractive order coupling caused by said first diffractive optical element.

18. A method of altering the fire of a gemstone comprising:
providing a gemstone that comprises diamond, said gemstone having a crown portion and a pavilion portion; and
forming a first diffractive optical element on or in said pavilion portion of said gemstone, said first diffractive optical element comprising a plurality of diffractive features spaced with respect to each other to diffract visible light,
wherein said first diffractive optical element comprises a first plurality of diffractive features having a first form factor, and further comprising forming a second diffractive optical element that comprises a second plurality of diffractive features having a second form factor, the second form factor being different than the first form factor.

19. A method of altering the fire of a gemstone comprising:
providing a gemstone that comprises diamond, said gemstone having a crown portion and a pavilion portion; and
forming a first diffractive optical element on or in said pavilion portion of said gemstone, said first diffractive optical element comprising a plurality of diffractive features spaced with respect to each other to diffract visible light,
wherein said first diffractive optical element comprises a first plurality of diffractive features having a first periodicity, and further comprising forming a second diffractive optical element that comprises a second plurality of diffractive features having a second periodicity, the second periodicity being different than the first periodicity.

20. The method of claim 19, wherein said first diffractive optical element comprises a diffraction grating.

21. The method of claim 20, wherein the period of said diffraction grating is in the range of 2 to 50 microns.

22. A method of altering the fire of a gemstone comprising:
providing a gemstone that comprises diamond, said gemstone having a crown portion and a pavilion portion; and
forming a first diffractive optical element on or in said pavilion portion of said gemstone, said first diffractive optical element comprising a plurality of diffractive features spaced with respect to each other to diffract visible light,
wherein said first diffractive optical element comprises a hologram.

23. A method of altering the fire of a gemstone comprising:
providing a gemstone that comprises diamond, said gemstone having a crown portion and a pavilion portion; and
forming a first diffractive optical element on or in said pavilion portion of said gemstone, said first diffractive optical element comprising a plurality of diffractive features spaced with respect to each other to diffract visible light,
wherein said first diffractive optical element comprises a two-dimensionally periodic or quasi-periodic array of separate diffractive features.

24. The method of claim 23, wherein said plurality of diffractive features of said first diffractive optical element comprise a tiled pattern.

* * * * *